(12) United States Patent
Orphanos et al.

(10) Patent No.: US 11,534,154 B2
(45) Date of Patent: Dec. 27, 2022

(54) DEVICES AND METHODS FOR TISSUE REPAIR

(71) Applicant: Medos International Sárl, Le Locle (CH)

(72) Inventors: Stephen J. Orphanos, Bridgewater, MA (US); Brian Otrando, Cumberland, RI (US); Kirsten H. Aarsvold, Quincy, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 386 days.

(21) Appl. No.: 15/692,720

(22) Filed: Aug. 31, 2017

(65) Prior Publication Data

US 2019/0059872 A1 Feb. 28, 2019

(51) Int. Cl.
 *A61B 17/04* (2006.01)
 *A61B 17/06* (2006.01)
 (Continued)

(52) U.S. Cl.
 CPC .... *A61B 17/0401* (2013.01); *A61B 17/06066* (2013.01); *A61B 17/0625* (2013.01);
 (Continued)

(58) Field of Classification Search
 CPC ........ A61B 17/0401; A61B 2017/0403; A61B 2017/0404; A61B 2017/0406; A61B 2017/0409; A61B 2017/0414; A61B 2017/042; A61B 2017/0422; A61B 2017/0424; A61B 2017/0475; A61B 2017/0496; A61B 2017/0417; A61B 2017/0458; A61B 2017/0464; A61B 2017/0477; A61B 2017/0425;
 (Continued)

(56) References Cited

U.S. PATENT DOCUMENTS

| 7,887,551 | B2 | 2/2011 | Bojarski et al. |
| 7,909,851 | B2 | 3/2011 | Stone et al. |
| 7,959,650 | B2 * | 6/2011 | Kaiser ................ A61B 17/0401 606/232 |
| 8,292,921 | B2 | 10/2012 | Stone et al. |
| 8,409,253 | B2 | 4/2013 | Stone et al. |

(Continued)

FOREIGN PATENT DOCUMENTS

| EP | 1568326 A1 | 8/2005 |
| EP | 2277455 A2 | 1/2011 |
| EP | 2446831 A2 | 5/2012 |

OTHER PUBLICATIONS

Extended European Search Report for EP App. No. 18191773.3 dated Jan. 24, 2019 (10 pages).

*Primary Examiner* — Katherine H Schwiker

(57) ABSTRACT

A tissue repair construct having first and second implants coupled via a flexible element is provided. The flexible element forms an adjustable loop closed with a sliding knot, and has first and second free ends extending from the knot formed by wrapping the second end around the first end. The second implant can have a changeable configuration. The construct can be placed within a surgical site in a patient's body such that the first implant is passed into a bone adjacent to soft tissue and the second implant is disposed on an opposed side of the soft tissue. The first free end of the flexible element is configured to be tensioned to decrease a size of the loop and thereby change the configuration of the second implant and to thereby cause at least the second implant to move towards the first implant.

8 Claims, 19 Drawing Sheets

(51) Int. Cl.
  *A61B 17/062* (2006.01)
  *A61B 90/00* (2016.01)
  *A61B 17/00* (2006.01)

(52) U.S. Cl.
  CPC .............. *A61B 2017/00004* (2013.01); *A61B 2017/042* (2013.01); *A61B 2017/0403* (2013.01); *A61B 2017/0404* (2013.01); *A61B 2017/0406* (2013.01); *A61B 2017/0409* (2013.01); *A61B 2017/0414* (2013.01); *A61B 2017/0417* (2013.01); *A61B 2017/0464* (2013.01); *A61B 2017/0475* (2013.01); *A61B 2017/0496* (2013.01); *A61B 2017/061* (2013.01); *A61B 2017/0608* (2013.01); *A61B 2090/062* (2016.02)

(58) Field of Classification Search
  CPC .... A61B 2017/0445; A61B 2017/0459; A61B 2017/0474; A61B 2017/0408; A61B 2017/0419; A61B 2017/0438; A61B 2017/0446–0453; A61B 2017/0456; A61B 2017/0461; A61B 2017/0462; A61B 2017/0466; A61B 2017/0454; A61B 2017/00663; A61B 17/0057; A61B 2017/00575; A61B 2017/00601; A61B 2017/00606; A61B 2017/0061; A61B 2017/00615; A61B 2017/00619; A61B 2017/00628; A61B 2017/00654; A61B 2017/00659; A61F 2/0811; A61F 2002/0817; A61F 2002/0823; A61F 2002/0835; A61F 2002/0841; A61F 2002/0874; A61F 2002/0852; A61F 2002/0858; A61F 2002/0865; A61F 2002/0882
  See application file for complete search history.

(56) References Cited

U.S. PATENT DOCUMENTS

| | | | |
|---|---|---|---|
| 8,562,647 B2 | 10/2013 | Kaiser et al. | |
| 8,608,777 B2 | 12/2013 | Kaiser et al. | |
| 8,790,369 B2 | 7/2014 | Orphanos et al. | |
| 8,828,053 B2 | 9/2014 | Sengun et al. | |
| 9,084,597 B2 | 7/2015 | Arai et al. | |
| 9,173,645 B2 | 11/2015 | Overes et al. | |
| 9,173,651 B2 | 11/2015 | Stone et al. | |
| 9,439,644 B2 | 9/2016 | Lizardi | |
| 2003/0130694 A1* | 7/2003 | Bojarski | A61F 2/0805 606/228 |
| 2005/0033363 A1* | 2/2005 | Bojarski | A61B 17/06166 606/228 |
| 2005/0107827 A1* | 5/2005 | Paprocki | A61B 17/0401 606/139 |
| 2008/0065114 A1* | 3/2008 | Stone | A61B 17/0401 606/139 |
| 2010/0268275 A1* | 10/2010 | Stone | A61B 17/0401 606/232 |
| 2010/0275432 A1 | 11/2010 | Pikus et al. | |
| 2011/0022061 A1* | 1/2011 | Orphanos | A61B 17/0401 606/139 |
| 2011/0022084 A1* | 1/2011 | Sengun | A61B 17/0469 606/228 |
| 2013/0237997 A1* | 9/2013 | Arai | A61B 17/0401 606/144 |
| 2014/0243893 A1* | 8/2014 | Santangelo | A61B 17/0401 606/232 |
| 2014/0336672 A1* | 11/2014 | Walters | A61B 17/0057 606/139 |
| 2015/0032157 A1 | 1/2015 | Dooney, Jr. et al. | |
| 2015/0272566 A1 | 10/2015 | Arai et al. | |
| 2016/0199053 A1 | 7/2016 | Norton et al. | |
| 2016/0199115 A1* | 7/2016 | Anderson | A61B 17/8869 606/232 |

* cited by examiner

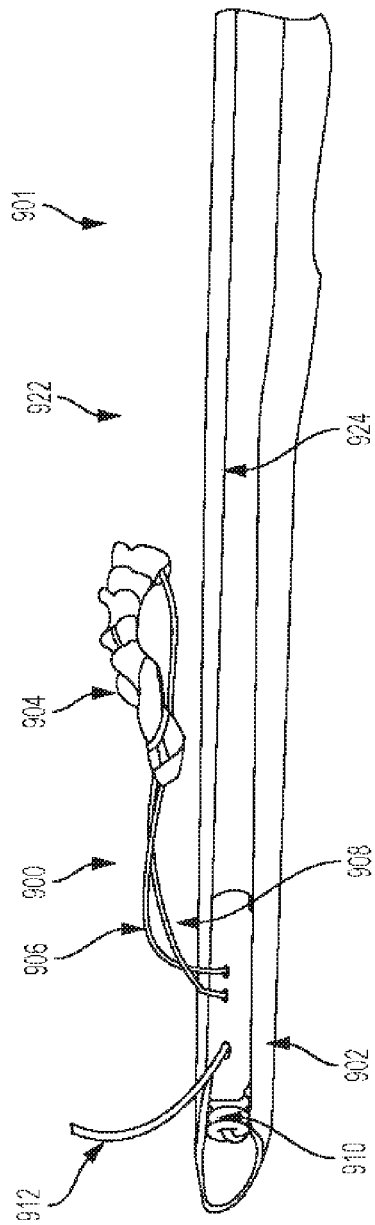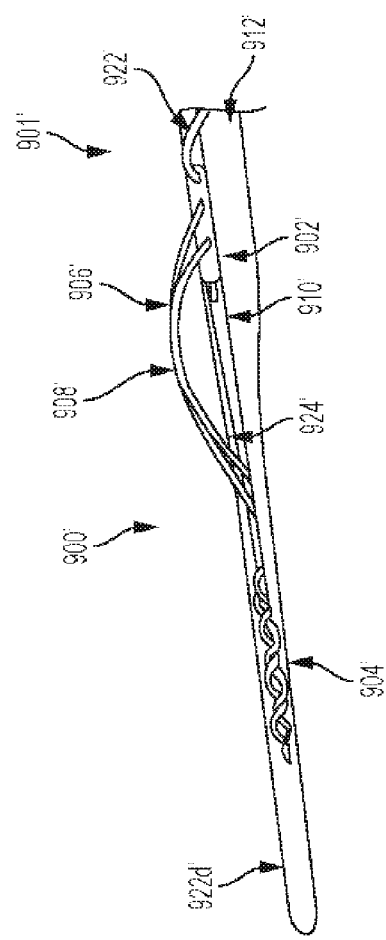
FIG. 7A
FIG. 7B

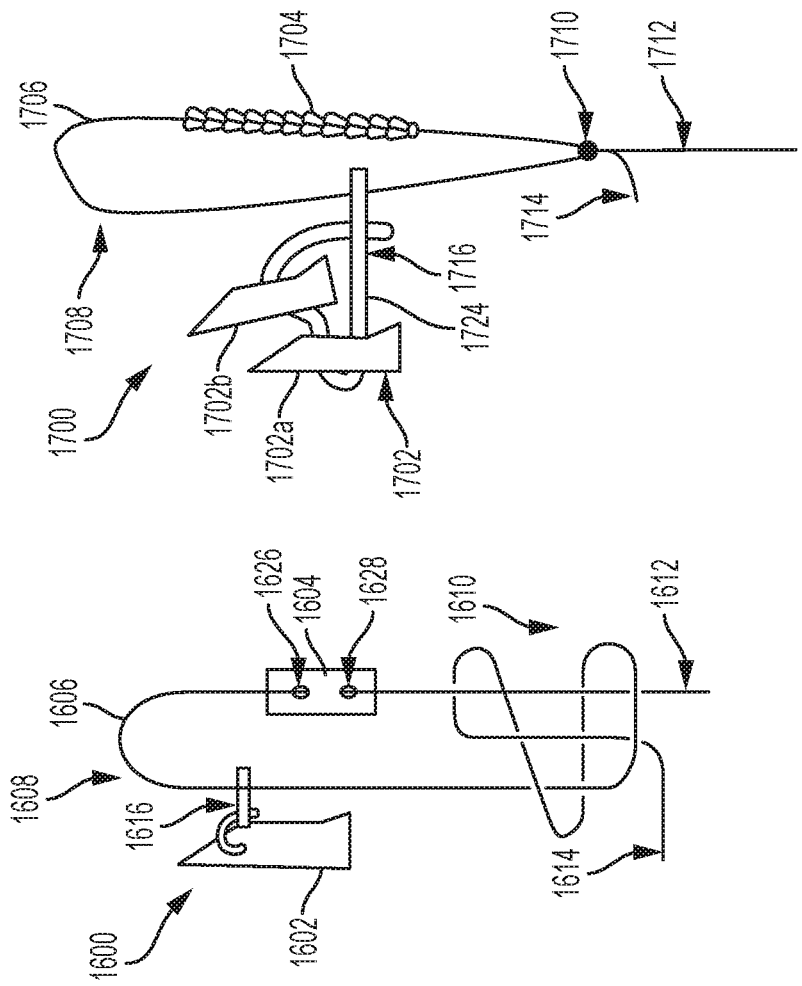
FIG. 12
FIG. 11
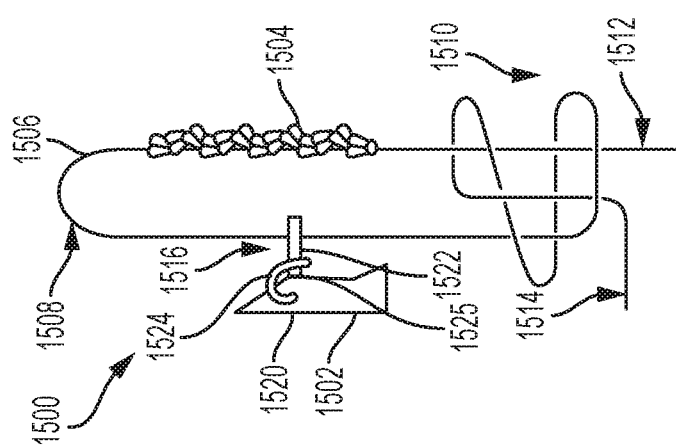
FIG. 10

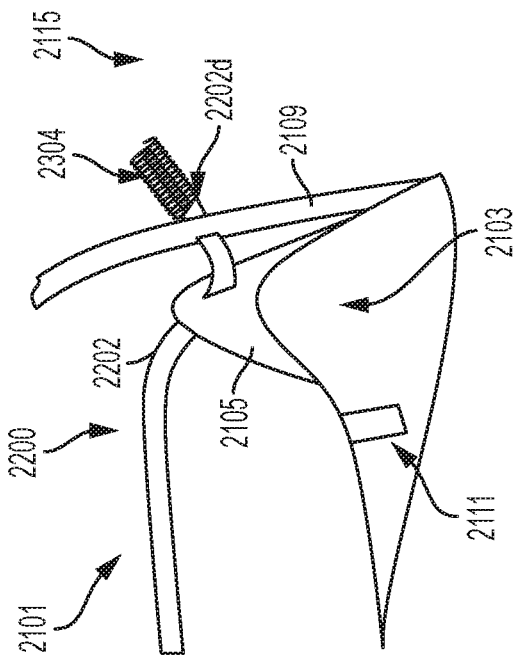
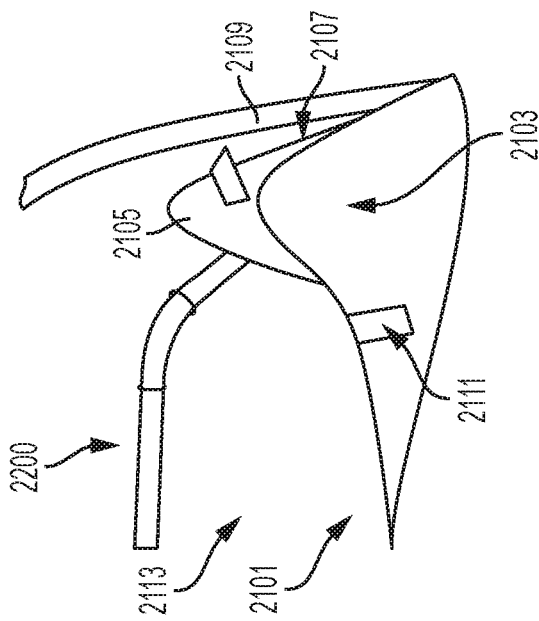

DEVICES AND METHODS FOR TISSUE REPAIR

FIELD

The present disclosure relates generally to devices and methods for knotless tissue repair.

BACKGROUND

A variety of injuries and conditions require repair of soft tissue damage, or reattachment of soft tissue to bone and/or surrounding tissue. For example, when otherwise healthy tissue has been torn away from a bone, such as a shoulder rotator cuff tendon being partially or completely torn from a humerus (a rotator cuff tear), surgery is often required to reattach the tissue to the bone, to allow healing and a natural reattachment to occur. A number of devices and methods have been developed for performing these surgical repairs. Some of the more successful methods including the use of suture fixation members, such as suture anchors, which typically include an anchor body having one or more suture attachment feature and include a tissue or bone engaging feature for retaining the suture anchor within or adjacent to the tissue or bone. Depending on the specific injury, one or more suture anchors connected to, or interconnected by, one or more segments of suture, may be used to perform the repair.

Surgery can also be required when a tear occurs in the substance of a single type of tissue, for example in the meniscus of the knee (a meniscal tear). One method of repairing such a tear is to stitch it closed by passing a length of suture through the tissue and tying the suture. Suture can also be used in conjunction with one or more suture anchors to repair such tissue tears. Sutures can be fastened to suture anchors and to tissue using knots tied by the surgeon during a repair procedure, or using "knotless" devices and methods, where one or more anchors and one or more sutures can be connected and tensioned without the surgeon needing to tie knots during the surgery. Knotless anchoring is of particular utility for minimally invasive surgeries, such as endoscopic or arthroscopic repairs, where the surgeon remotely manipulates the suture at the surgical site using tools inserted through a small percutaneous incision, small diameter cannula, or an endoscopic tube, which can make the knot-tying process difficult and tedious.

While many suture anchoring systems have been developed for repairing torn or otherwise damaged tissue, there are certain drawbacks. For example, a surgical procedure, such as a shoulder instability repair, can involve multiple steps where a suture is passed in a somewhat cumbersome manner, knots may potentially need to be tied, and other steps may need to be taken that complicate and prolong the surgical procedure and may thus affect its outcome.

Accordingly, there remains a need for improved tissue repair devices, systems, and methods.

SUMMARY

In general, a system and method for deploying a surgical construct at a surgical site are provided.

In one aspect, a surgical device is provided that in some embodiments includes a first implant, a second implant having a changeable configuration, and a flexible element coupling the first and second implants, the flexible element forming an adjustable loop closed with a sliding knot, and having first and second free ends extending from the knot. The first free end of the flexible element is configured to be tensioned to decrease a size of the loop and thereby change the configuration of the second implant.

The surgical device can have any number of variations. For example, the sliding knot can be formed by wrapping the second free end of the flexible element around the first free end of the flexible element. As another example, the first implant can be coupled to the loop via a coupling feature.

In some embodiments, the first implant can be substantially rigid and the second implant can be substantially non-rigid and conformable. In some embodiments, the first and second implants can be substantially rigid. In some embodiments, the first and second implants can be substantially non-rigid and conformable. In some embodiments, the first and second implants can be slidably coupled to the loop.

The second implant can vary in many ways. For example, the second implant can include or can be a member formed along a length of the loop such that a decrease in the size of the loop causes the second implant to reduce a length thereof and increase a diameter thereof. In some embodiments, the member can be formed from a suture strand wrapped around the portion of the loop.

In some embodiments, the surgical device can further include a third implant having a changeable configuration and a second flexible element forming a second adjustable loop closed with a second sliding knot and having third and fourth free ends. The second flexible element can have the third implant coupled thereto, and the third free end can be configured to be tensioned to decrease a size of the second loop and thereby change the configuration of the third implant. The first implant can be coupled to the second loop.

In another aspect, a surgical assembly for attaching tissue to bone is provided that in some embodiments includes a delivery device and a deployable implant construct. The delivery device can have a shaft with a tissue penetrating distal tip, the shaft having a longitudinal channel extending through a sidewall thereof along at least a portion of a length of the shaft. The deployable implant construct can have a first implant associated with the delivery device, a second implant having a changeable configuration, and a flexible element coupling the first and second implants, the flexible element forming an adjustable loop closed with a sliding knot and having first and second free ends extending from the sliding knot. The first free end of the flexible element can be configured to be tensioned to decrease a size of the loop and thereby change the configuration of the second implant.

The system can have any number of variations. For example, the first implant can be removably disposed within the channel of the shaft and the second anchor can be disposed outside of the channel. As another example, the first and second implants can be removably disposed within the channel of the shaft. In some embodiments, the delivery device can include a needle having the tissue penetrating distal tip and the longitudinal channel.

In yet another aspect, a surgical method is provided that in some embodiments includes advancing into a surgical site a construct having a first implant, a second implant, and a flexible element forming a loop having a pre-tied sliding knot and coupling the first and second implants, placing the construct within the surgical site such that the first implant is passed into a bone adjacent to soft tissue and on a first side of the soft tissue, and the second implant is disposed on a second, opposed side of the soft tissue, and tensioning a loose end of the flexible element extending from the sliding knot to cause the flexible element to slide through the sliding knot to decrease a size of the loop and change a configuration of the second implant to thereby cause at least the second implant to move towards the first implant.

The method can vary in many ways. For example, tensioning the suture can include pulling the first terminal end suture to thereby lock the sliding knot. As another example, the second anchor can change the configuration such that at least one dimension of the second anchor decreases. The at least one dimension can include, for example, a length of the second anchor.

In some embodiments, placing the construct within the surgical site can include penetrating the tissue with a distal tip of a needle of a surgical instrument having the construct removably associated therewith such that the distal tip is passed from the second side of the soft tissue to the first side of the soft tissue and is advanced into the bone to deploy the first anchor into the bone, wherein the second anchor is deployed on the second side of the tissue as the distal tip passes from the second side to the first side.

In other embodiments, placing the construct within the surgical site can include penetrating the tissue with a distal tip of needle of a surgical instrument having the construct removably associated therewith such that the distal tip passes from the first side of the soft tissue to the second side of the soft tissue to deploy the second anchor on the second side, retracting the needle to the first side, and advancing the distal tip of the needle into the bone to deploy the first anchor into the bone.

BRIEF DESCRIPTION OF DRAWINGS

This disclosure will be more fully understood from the following detailed description taken in conjunction with the accompanying drawings, in which:

FIG. 7A is a perspective view of a distal portion of yet another embodiment of a delivery device;

FIG. 7B is a perspective view of a distal portion of yet another embodiment of a delivery device;

FIG. 10 is a perspective schematic view of one embodiment of a surgical device;

FIG. 11 is a perspective schematic view of another embodiment of a surgical device;

FIG. 12 is a perspective schematic view of yet another embodiment of a surgical device;

FIG. 17A is a side schematic view illustrating one embodiment of a method of tissue repair in a shoulder joint of a patient;

FIG. 17B is another side schematic view illustrating the method of FIG. 17A;

DETAILED DESCRIPTION

Figure 2:
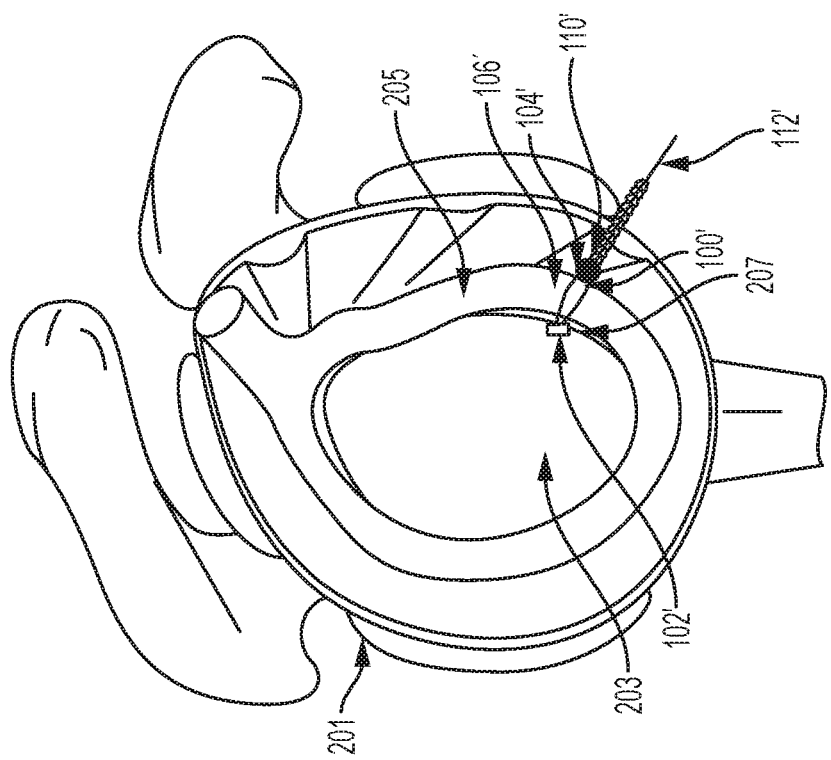
FIG. 2 is a side cross-sectional view of a shoulder joint having a surgical device implanted thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used. In addition, "substantially" is defined as a range based on manufacturing variations and variations over temperature and other parameters.

In general, a tissue repair construct, also referred to herein as a surgical device, is provided. The tissue repair construct includes first and second implants, or suture anchors, coupled via a flexible element, such as, for example, a suture. The flexible element forms an adjustable loop having the first and second implants coupled thereto and closed via a sliding knot, and the flexible element has first and second free ends extending from the knot. The sliding knot can be formed by wrapping the second free end around the first free end such that the first free end is a tensioning, or post limb, end.

The tissue repair construct can be deployed in a way that involves a reduced number of steps as compared to existing tissue repair approaches using suture anchors. In particular, a delivery device, such as a suture passer or needle, can be used to deploy one of the implants into a bone at a surgical site on one side of soft tissue, and deploy another one of the implants on the second, opposed side of the soft tissue. The adjustable loop of the flexible element can thus span the soft tissue that has the first and second implants on the opposed sides thereof. Once the implants are positioned as desired, the first free ends of the flexible element, which extends from the surgical site such that it is accessible to a surgeon, can be tensioned to cause the flexible element to slide through the sliding knot and thereby decrease a size of the loop such that at least the second implant moves towards the first implant, thereby approximating the soft tissue to the bone. In some embodiments, the second implant can have a changeable configuration such that the configuration changes when the first free end is tensioned.

The surgical devices described herein can be deployed using a suitable delivery device. For example, a distal portion, such as a part of a shaft of the delivery device or a needle coupled to the shaft, has a longitudinal channel extending through a sidewall thereof along at least a portion of a length thereof. The longitudinal channel is able to seat one or more of the implants of the surgical device. In some embodiments, the channel seats a first implant that is configured to be implanted into a bone, while a second implant, coupled to the first implant via an adjustable loop and configured to be deployed on the peripheral side of the soft tissue, is disposed outside of the channel seating the first implant. The second implant is able to be deployed in a simplified, "passive" manner, whereby the second implant becomes disassociated from the delivery device at the site of its implantation on one side of a soft tissue when the delivery device is moved to another side of the soft tissue. Thus, the act of passing a distal end of the delivery device to a side of the soft tissue where the first implant is deployed into a bone at a desired location, also includes substantially simultaneously deploying the second implant on the opposed side of the soft tissue. "Passive" deployment of the second anchor can alternately occur as the delivery device is removed from the joint space, whereby the delivery device passes through soft tissue prior to deploying the first implant into bone at a desired location, and the second implant becomes disassociated from the delivery device as the delivery device is removed from the joint after tracing back through its path. Thus, the act of removing the delivery device also includes substantially simultaneously deploying the second implant on the opposed side of the soft tissue. Once the implants are deployed in this manner, all that is then required is to tension one free end of the flexible element to adjust a size of the loop, e.g., based on anatomical characteristics of the surgical site, extend of a defect being repaired, and/or other factors.

Accordingly, the described techniques provide a system for tissue repair having a reduced number of components. The system can be used by a surgeon in a simplified manner as compared to conventional systems, since no additional instruments are required to pass a suture and deploy suture anchors in a desired manner. Furthermore, the described techniques allow performing suture passing and implant deployment as part of the same step. Because a separate step of suture passing is simplified or eliminated, a surgical procedure (e.g., a shoulder instability repair) can be performed more quickly and with a reduced number of operations. Also, the described techniques provide improved control over tension of a flexible element of an implantable construct. While existing systems may not permit tensioning of an operative suture after the anchor has been implanted into a bone, the tissue repair construct described herein allows tensioning the flexible element after at least one of the implants has been implanted into a bone.

First and second implants of a surgical device can have many different forms. For example, the first implant can be substantially rigid and the second implant can be substantially non-rigid and conformable. In other embodiments, however, both of the first and second implants can be rigid or non-rigid and conformable. Each of the first and second implants may be in the form of two or more implants, including a different number of implants.

Figure 1:
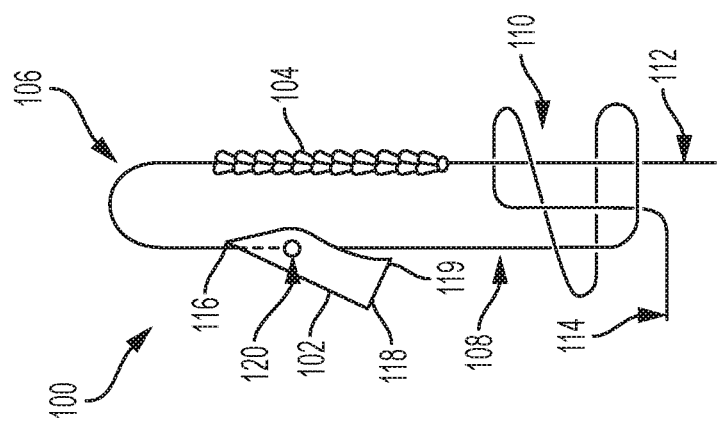
FIG. 1 is a perspective schematic view of one embodiment of a surgical device.

FIG. 1 illustrates one embodiment of a tissue repair construct or surgical device 100 that includes a first implant 102 and a second implant 104 having a changeable configuration. The surgical device 100 also has a flexible element 106 coupling the first and second implants 102, 104. As shown in FIG. 1, the flexible element 106 forms an adjustable loop 108 closed with a sliding knot 110, and having first and second tails or free ends 112, 114 extending from the knot 110. As shown, the first and second implants 102, 104 are coupled to the adjustable loop 108.

It should be noted that, in FIG. 1, the sliding knot 110 is shown in a loose configuration for illustration purposes only. In the ready-to-deploy configuration (e.g., in which the surgical device 100 is associated with a suitable delivery device), the sliding knot 110 formed by the flexible element 106 is in the form of a tighter, pre-tied knot. In the illustrated embodiments, the sliding knot 110, as well as other sliding knots described herein, can be formed as disclosed, for example, in U.S. Pat. No. 8,828,053, entitled "Methods and devices for repairing and anchoring damaged tissue," which is hereby incorporated by reference in its entirety. It should be appreciated, however, that sliding knot 110 can be formed in variety of other ways. The sliding knot 110 is formed such that the second free end 114, which can also be referred to as a locking end, is looped around the first free end 112, which can also be referred to as a post limb. It should be appreciated that the sliding knot 110, as well as other sliding knots described herein, are shown to be formed in a certain way by way of example only. Any other suitable types of sliding locking knots can be used. Also, in this embodiment, as well as in other implementations described herein, the sliding knots are formed such that they cannot pass or break through the implants prior to or after the implant deployment.

The first free end 112 is configured to be tensioned to decrease a size of the loop 108 and thereby change the configuration of the second implant 104. The flexible element 106 can be in the form of a suture or any other flexible element.

The first and second implants 102, 104 can have any number of various configurations. For example, as in the illustrated embodiment, the first implant 102 can be substantially rigid, whereas the second implant 104 can be substantially non-rigid and conformable. The first implant 102 can have any suitable shape. For example, as in the example of FIG. 1, it can be generally cylindrical and one of its shorter sides 116 can be in the form of a sharp, tapered end, while its other, opposed shorter side 118 can be generally flat, though the side 118 can have other features, such as a protruding edge 119. The features such as, for example, the tapered end 116 and edge 119 can facilitate engagement of the implant 102 with bone. Also, one or more of these or other features can have a cutting surface. It should be appreciated that first implant 102 can have any other suitable shape, including a generally cylindrical shape. The first implant 102 can be substantially rigid or it can be substantially non-rigid and conformable. The longer and shorter sides of the first implant 102 can be symmetrical or asymmetrical and, additionally or alternatively, they can have any other features, such as one or more protruding or depressed features.

In the illustrated example, the flexible element 106 passes through the first implant 102 at one location 120 such that the first implant 102 is coupled to the loop 108 at this single location. It should be appreciated, however, that in other embodiments the flexible element can pass through the first implant in more than one location at the first implant. Also, in some embodiments, the first implant can be coupled to the loop via a coupling feature, or in other manners. The first implant 102 can be slidably coupled to the flexible element 106. However, in some embodiments, the first implant 102 can be fixedly coupled to the flexible element 106; for example, a portion of the flexible element 106 can be attached to the first implant 102 by crimping, adhesion with an adhesive, being tied around the implant 102, etc.

The second implant 104 can have various configurations. In the illustrated example, as mentioned above, the second implant 104 is substantially non-rigid and conformable. As shown in FIG. 1, the second implant 104 can be in the form of a member formed along a length of the loop 108 such that a decrease in the size of the loop 108 causes the second implant 104 to reduce a length thereof and increase a diameter thereof. For example, the second implant 104 can be formed from a suture strand (which can be separate from the flexible element 106) that is wrapped around the portion of the loop 108. The suture strand can be wrapped around the portion of the loop 108 in any suitable manner such that the suture strand can bunch up or otherwise change its configuration and thus increase its diameter. For example, the suture can be intertwined, knitted, weaved around the around the portion of the loop 108, or otherwise manipulated to form the second implant 104. The second implant 104 can be formed in an accordion-like manner such that it can be collapsed into a wider (in diameter) and shorter configuration when the second implant 104 is caused to push against tissue and/or post limb 112 is pulled as discussed below. In some embodiments, the second implant 104 can be formed similar to anchor bodies disclosed in U.S. Pat. No. 9,173,645, entitled "Anchor assembly including expandable anchor," which is hereby incorporated by reference in its entirety.

In the illustrated embodiment, the first and second implants 102, 104 are slidably coupled to the loop 108, though it should be appreciated that in other embodiments at least the first implant can be fixedly attached to the loop 108. It should be appreciated that first and second implants of a surgical device in accordance with the described techniques can vary in many ways. For example, as discussed in more detail below, each of the first and second implants can include two or more respective implants. In some embodiments, the first implant can encompass two or more implants whereas the second implant can be a single implant. In other embodiments, the first implant can be a single implant, and the second implant can encompass two or more implants.

The first implant and the second implant can include the same or a different number of respective implants, and each of the implants can be substantially rigid or substantially non-rigid and conformable. For example, in some embodiments, the first implant can be substantially rigid and the second implant can be substantially non-rigid and conformable. As another example, in some embodiments, the first and second implants can be substantially rigid. As a further example, in some embodiments, the first and second implants can be substantially non-rigid and conformable. The implants can be coupled to a loop directly (e.g., a portion of the loop can pass therethrough at one or more locations) or via a coupling member. Furthermore, in some embodiments, two or more devices can be coupled to one another via a first implant. For example, each of the devices can include a flexible element and a second implant having a changeable configuration, and the devices may share the first implant such that the separate flexible elements of the devices are coupled to the same first implant.

In the illustrated embodiments, the surgical device, such as surgical device 100 of FIG. 1, can be positioned in a surgical site in a patient's body such that a first implant is positioned in a bone adjacent to soft tissue that is being attached to the bone, and a second implant is positioned on a second, opposed side of the soft tissue. The configuration of the second implant can be changed by tensioning a loose end of the flexible element extending from the sliding knot to cause the flexible element to slide through the sliding knot to decrease a size of the loop and thereby change the configuration of the second implant.

Although the surgical method is discussed in more detail below, FIG. 2 illustrates generally one embodiment of a surgical device 100' (which can be similar to device 100 of FIG. 1) deployed in a shoulder joint 201 to repair a labral tear 207. The tear 207 can be Bankart labral tear, a SLAP (superior labral tear from anterior to posterior) tear, or any other tear. The surgical device 100' can be deployed, using a suitable delivery device, via a reduced number of steps, as also discussed below. As shown in FIG. 2, the surgical device 100' having first and second implants 102', 104' coupled via a flexible element 106' forming a loop and a sliding knot 110', can be positioned such that the first implant 102' is disposed in a glenoid 203 on one side of a labrum 205. The second implant 104' in the changed configuration is disposed on the opposed side of the labrum 205. When a terminal end 112' (which can be similar to terminal end 112 of flexible element 106 of FIG. 1) extending from the sliding knot 110' is tensioned, the flexible element 106' slides through the sliding knot 110' to thereby decrease a size of the loop and change a configuration of the second implant 104'. In this way, the second implant 104' moves towards the first implant 102' to attach the labrum 205 to the glenoid 203 and thereby repair the tear 207.

Figure 3:
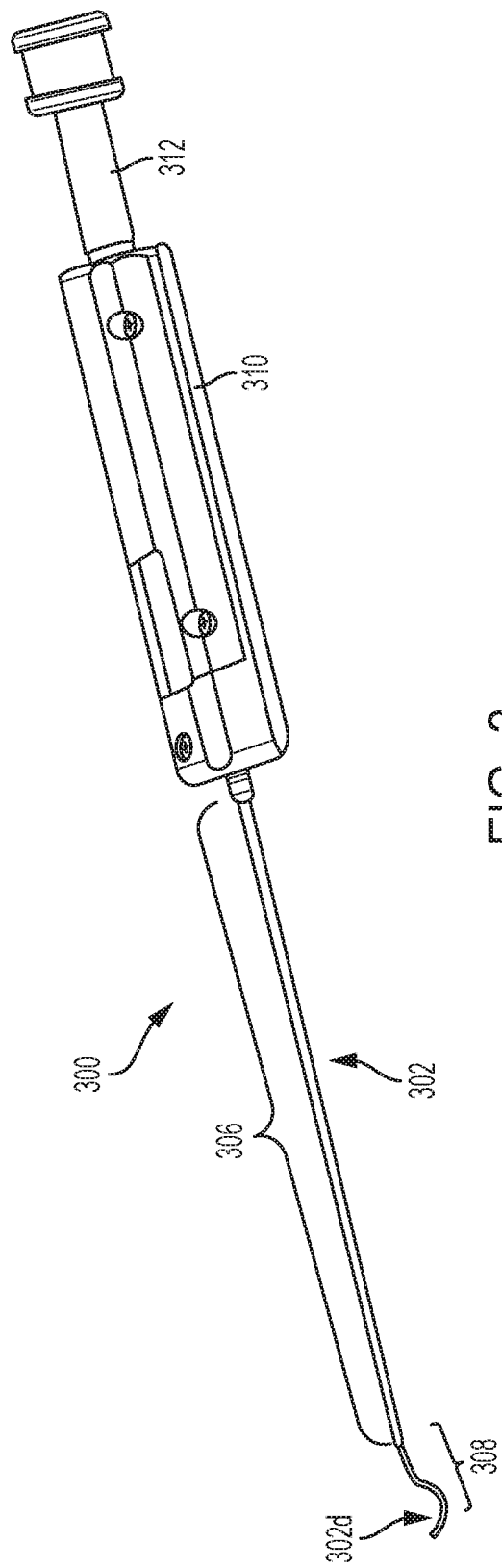
FIG. 3 is a perspective view of one embodiment of a delivery device.

A surgical assembly for attaching tissue to bone using the described surgical device can include any suitable delivery device. FIG. 3 illustrates one embodiment of a delivery device 300 having a shaft 302 with a tissue penetrating distal tip 302d. At least a portion of the shaft 302 has a longitudinal channel 304 extending through a sidewall thereof along at least a portion of a length of the shaft 302. In the illustrated embodiment, as shown in FIG. 3, the shaft 302 has a central portion 306 and a needle 308 extending distally from the central portion 306. Thus, in this example, the needle 308, which can be a separate component coupled to the central portion 306 or which can be formed integrally and/or monolithically with the central portion 306 of the shaft 302, has the longitudinal channel 304 extending through a sidewall thereof and a distal tip 308d that coincides with the tissue penetrating distal tip 302d of the shaft 302.

Figure 4:
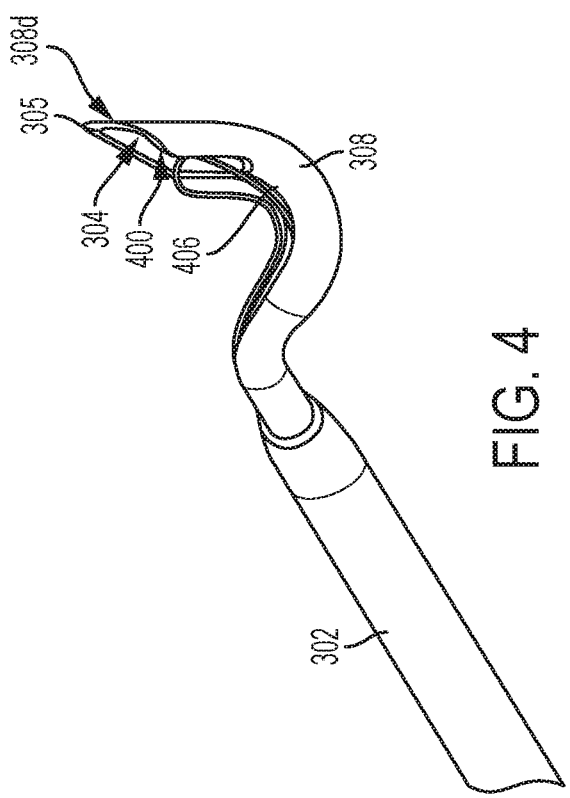
FIG. 4 is a perspective view of a distal portion of the delivery device of FIG. 3.

The longitudinal channel 304 extending along at least a portion of a length of the needle 308 can removably seat at least one of first and second implants of a surgical device (e.g., surgical device 100 of FIG. 1, or any other device). Thus, FIG. 4 illustrates that the channel 304 of the needle 308 seats a surgical device 400 having first and second implants (obscured) coupled via a flexible element 406 in the form of a suture. At least a portion of the flexible element 406 can extend beyond the channel 304, as schematically shown in this example. Also, the second implant (e.g., an implant similar to second implant 104 in FIG. 1) can be disposed outside of the channel 304 and, in some embodiments, within a sheath or other enclosure associated with the shaft of the delivery device.

It should be appreciated that, as mentioned above, the needle 308 is shown by way of example only, as a longitudinal channel configured to seat at least one of the implants of a surgical device that can be formed in a distal portion of the shaft of a delivery device, the shaft having a distal tissue penetrating tip. Furthermore, the needle, which can be coupled distally to the shaft or can be part of the shaft, can have a variety of configurations. For example, the needle can be straight, curved, helical, corkscrew-type or it can have any other suitable configuration suitable for certain surgical procedures and for passing at various anatomical locations. A distal tip of the needle can also be configured many various ways. For example, in at least one embodiment, as shown in FIG. 4, the distal tip 308d of the needle 308 can be angled, with a substantially flat distal-most surface 305.

Referring back to FIG. 3, the delivery device 300 can have a proximal handle 310 having the shaft 302 extending distally therefrom. An actuator 312 coupled proximally to the proximal handle 310 can be configured to be activated to deploy the surgical device 400. For example, the delivery device 300 can include one or more pusher rods or other actuating elements configured to advance one or more of the surgical device's implants distally along the channel seating the implant(s) and out of engagement with the delivery device 300. In embodiments in which both the first and second implants are loaded onto the needle of the delivery device, the delivery device can be activated to "actively" deploy both of the first and second implants, which can be done in any order. Depending on an implementation, the same pusher rod can be used to deploy both of the first and second implants, or each of the first and second implants can be deployed using a respective pusher rod. For example, the implants can be disposed at different levels in the needle and a separate pusher rod can be actuated to advance each implant distally. In addition, the delivery device 300 can have depth indicators configured to indicate a depth of insertion of implants. For example, one or more depth indicators (e.g., marks) can be disposed on at least one of the shaft 302 or actuator 312. In some embodiment, the handle 310 can have windows or other openings providing visual access to depth indicators.

In embodiments in which, in a pre-deployed configuration, one of the first and second implants is disposed outside of the needle (i.e., it is not seated in the needle's channel), such an implant can be "passively" deployed whereas the implant seated in the channel can be deployed actively or "passively", as discussed in more detail below.

Figure 5:
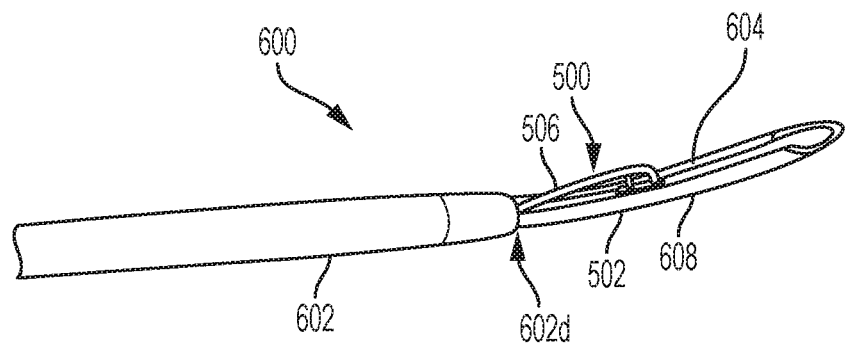
FIG. 5 is a perspective view of a distal portion of one embodiment of a delivery device.

A surgical device can be removably associated with a needle in a number of ways. For example, at least one of the first and second implants can be seated in a longitudinal channel extending through a sidewall of the needle. As mentioned above, as shown in FIG. 4, each of the implants of the surgical device 400 can be seated in the channel 304. FIG. 5 illustrates an embodiment of a distal portion of a delivery device 600 having a shaft 602 and a needle 608 extending distally from the shaft 602. As shown, a longitudinal channel 604 extending through the needle 608 has a surgical device 500 removably seated therein. In particular, in this example, a first implant 502 is seated in the channel 604, while a second implant (not shown) coupled to the first implant 502 via a flexible element 506 can be disposed within a lumen (not shown) of the shaft 602. However, in other implementations, the second implant, such as an implant having a changeable configuration, can also be seated in the channel 604 proximally to the first implant 502. As shown in FIG. 5, the flexible element 506 extends underneath a distal end 602d of the shaft 602. In this example, the flexible element 506 is coupled to the first implant 502 at two locations at the first implant 502, though it should be appreciated that the flexible element can be coupled to the first implant at one or more than two (e.g., three, etc.) locations, as the described techniques are not limited in this respect. Although not shown in FIG. 5, like surgical device 100 of FIG. 1, the surgical device 500 has a loop with a sliding locking knot formed by coupling terminal ends of the flexible element 506 to one another.

Figure 6:
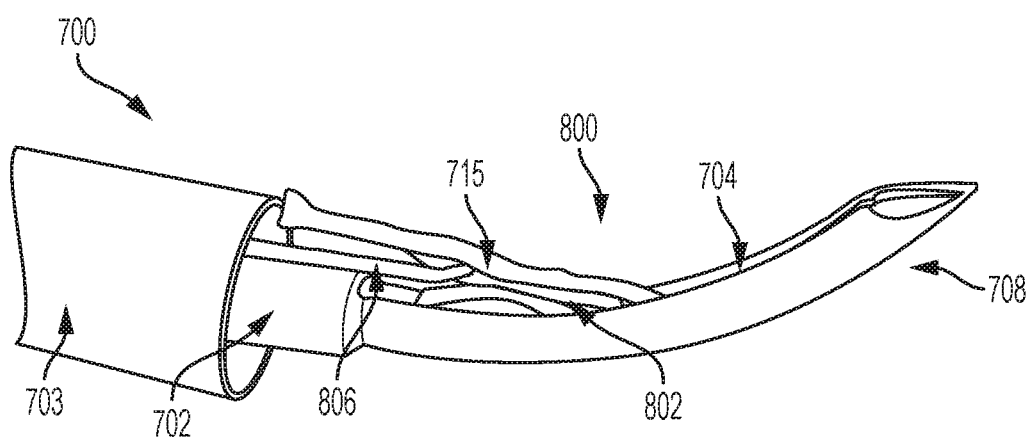
FIG. 6 is a perspective view of a distal portion of another embodiment of a delivery device.

FIG. 6 illustrates an embodiment of a distal portion of a delivery device 700 having a shaft 702 and a needle 708, which can be part of the shaft, extending distally from the shaft 702. As shown, a longitudinal channel 704 extending through the needle 708 has a surgical device 800 removably seated therein. In particular, in this example, a first implant 802 is seated in the channel 704, while a second implant (not shown), coupled to the first implant 802 via a flexible element 806 and disposed outside of the channel 704, can be disposed within an outer sheath 703 having at least a portion of the shaft 702 disposed therethrough. The outer sheath 703 can protect the second implant until the second implant is deployed at a desired location. As shown in FIG. 6, the flexible element 806 extends underneath the sheath 703. The outer sheath 703 can be removable such that, after the first implant 802 is actively deployed, and before the second implant is passively deployed, the sheath 703 can be removed. In other embodiments, the sheath 703 can be configured such that it can be moved proximally to expose the second implant seated within its lumen. The sheath 703 can be a component separate from the shaft 702 or, in some embodiments, the sheath 703 can be part of the shaft 702. In this embodiment, the first implant 802 can be coupled to the flexible element 806 via a suture strand 715. Although not shown in FIG. 6, like surgical device 100 of FIG. 1, the surgical device 800 has a loop with a sliding locking knot formed by coupling terminal ends of the flexible element 806 of the surgical device 800 to one another.

In some embodiments, as mentioned above, at least a portion of a surgical device can be removably associated with a distal portion of a surgical device's shaft. For example, in some embodiments, one of the implants, such as a first implant configured to be deployed into a bone, can be seated in a bore or channel in the delivery device's shaft, whereas another, second implant can be disposed outside of the channel of the shaft. In this way, during deployment, the second implant can be passively deployed. FIG. 7A illustrates an embodiment of a distal portion of a delivery device 901 having a shaft 922 that has a longitudinal channel 924 extending through a sidewall thereof along at least a portion of a length of the shaft 922. In this example, a surgical device 900 is coupled to the shaft 922 such that a first implant 902 is seated in the channel 924, while a second implant 904 coupled to the first implant 902 via a flexible element 906 is disposed outside of the channel 924 of the shaft 602.

The flexible element 906 forms an adjustable loop 908 closed with a sliding knot 910, and having tails or free ends extending from the knot, with one of the ends, a free end 912, shown partially. In this example, the first implant 902 can be substantially rigid, whereas the second implant 904 can be substantially non-rigid, conformable, and having a changeable configuration. Other configurations of the implants are possible, e.g., the first implant can be at least partially non-rigid. The surgical device 900 can be deployed by actively deploying the first implant 902 (e.g., by activating a pusher rod of the delivery device 901) and passively deploying the second implant 904 once the second implant 904 is retracted from a joint, as discussed below.

In some embodiments, both first and second implants of a surgical device can be seated in a channel of the delivery device's shaft (or a needle extending therefrom). The first and second implants, each of which may be in the form of more than two implants, can be seated in the channel in any suitable way. For example, the second implant having a changeable configuration can be distal relative to the first implant. The first and second implants can be spaced apart along the channel or they can be adjacent to one another. FIG. 7B illustrates an embodiment of a distal portion of a delivery device 901' having a shaft 922' that has a longitudinal channel 924' extending through a sidewall thereof along at least a portion of a length of the shaft 922'. In this example, a surgical device 900' (which can be similar to surgical device 900 of FIG. 7A) is coupled to the shaft 922' such that both first and second implants 902', 904' coupled via a flexible element 906' are seated in the channel 924'. The flexible element 906' forms an adjustable loop 908' closed with a sliding knot and 910' having free ends extending from the knot 910', with a first end 912' configured to be tensioned shown in FIG. 7B.

As shown in FIG. 7B, the second implant 904' is seated in the channel 924' closer to a distal end 922d' of the shaft 922' than the first implant 902', and the first and second implants 902', 904' are spaced apart from one another. However, it should be appreciated that, as mentioned above, the implants can be seated in the channel in any suitable relation to one another. In this example, like in the example of FIG. 7A, the first implant 902' can be substantially rigid, whereas the second implant 904' can be substantially non-rigid, conformable, and having a changeable configuration; though other configurations of the implants are possible (e.g., the first implant can be non-rigid). The surgical device 900 can be deployed by actively deploying the first implant 902' (e.g., by activating a pusher rod of the delivery device 901') and actively deploying the second implant 904' (e.g., by activating the same or different pusher rod of the delivery device 901' that is used to deploy the first implant 902').

Figure 7C:
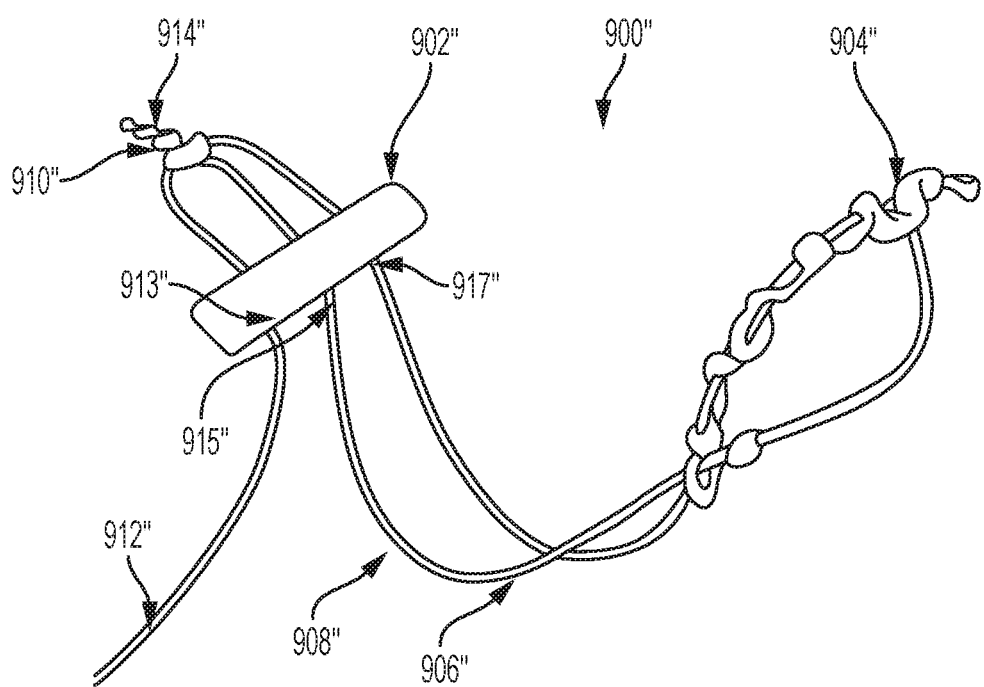
FIG. 7C is a perspective view of one embodiment of a surgical device.

FIG. 7C illustrates an embodiment of a surgical device 900", which can be similar to surgical devices 900, 900' in FIGS. 7A and 7B, respectively. As shown, the surgical device 900" has first and second implants 902", 904" coupled via a flexible element 906" that forms an adjustable loop 908" closed with a sliding knot 910" and having first and second free ends 912", 914" extending from the knot 910". In this example, the knot 910" is disposed adjacent to the first implant 902", and the first free end 912" is configured to be tensioned to decrease a size of the loop 908" and thereby change a configuration of the second implant 904". In this example, the flexible element 906" passes through the first implant 902" at three locations of the implant 902"—at three through openings 913", 915", 917" in the body of the first implant 902", though it should be appreciated that this configuration is shown by way of example only.

It should further be appreciated that particular devices are shown in FIGS. 7A-7C by way of example only. A surgical device 100 of FIG. 1, or any of the other surgical devices described herein, can be removably associated with a shaft of a delivery device as shown in FIGS. 7A and 7B, or in other manners.

In general, implants discussed herein, which can also be referred to as anchors, are configured to be implanted in a body of a patient. The implants are configured to be coupled via a flexible element that can be in the form of any suitable suture. For example, the suture can be a DYNACORD® suture, though any other type of suture can be used additionally or alternatively. A surgical device having the implants can be used in a tissue repair procedure, e.g., an arthroplasty at a joint such as the shoulder, knee, or tip, a rotator cuff repair procedure for repairing a torn rotator cuff at a shoulder, a meniscal repair procedure for repairing a meniscal tear at a knee, etc.

The first and second implants can be made from any of a variety of materials. The implants can be absorbable or non-absorbable. For example, a first implant, which can be at least partially rigid, can be made from polyether ether ketone (PEEK), Polylactic acid or polylactide (PLA), BIOCRYL® RAPIDE®, collagen, stainless steel, etc. Such an implant can be formed by a variety of techniques, for example by an injection molding process such as overmolding or by a post-molding process such as post-molding machining. The implant can have any of a variety of sizes as appropriate for, e.g., use at a particular anatomical location and with a particular patient.

The second implant, such as, for example, a substantially non-rigid and conformable member, can be formed from a suitable suture. For example, the suture can be a partially bioabsorbable, high strength suture comprising ultra high molecular weight polyethylene (UHMWPE) and polydioxanone (PDS). In some embodiments, the suture can be an ORTHOCORD® suture, a DYNACORD® suture, or any other type of suture. Also, the second implant can be formed from a tape, fabric, or any other conformable material. In some embodiments, the material from which the second implant is made (e.g., a suture) can be coated or otherwise associated with a material that promotes tissue growth and healing.

As mentioned above, the second implant can be formed by intertwining, braiding, wrapping around, knitting, or otherwise coupling its material around a portion of a flexible element coupling the second implant to the first implant. In some embodiments, the second implant can be formed from collagen or other similar material. The second implant can be at least partially absorbable. It should be appreciated that each of the first and second implants can be either substantially rigid or substantially non-rigid. Also, each of the first and second implants can encompass one or more respective implants.

A surgical device as described herein can be deployed using a delivery device (which can also be referred to as suture passer device) in various ways. Depending on the configuration of the surgical device and the way in which it is associated with the delivery device, at least one of the surgical device's implants can be deployed actively. FIGS. 8A-8D illustrate an embodiment of a method of deploying a surgical device at a surgical site such that one of implants of the surgical device is deployed actively while another of the implants is deployed passively. The surgical device is implanted at a shoulder joint 1001 (glenohumeral joint) of a patient during a surgical procedure to repair a defect or tear 1007. The tear 1007 can be, for example, torn labrum and/or capsule, such as the Bankart lesion. A variety of other tears can be repaired using the described method as well.

In the example of FIGS. 8A-8D, a delivery device 1100 is shown schematically to deliver a surgical device, also referred to herein as a tissue repair construct, 1200 (not shown in FIG. 8A) to the surgical site. The delivery device 1100 has a shaft 1102 with a distal tip 1102*d* that is configured to penetrate through tissue, and with a longitudinal channel configured to seat at least one implant of the surgical device 1200. A distal portion of the shaft can be in the form of a needle (e.g., needle 308 in FIGS. 3 and 4).

Figure 8B:
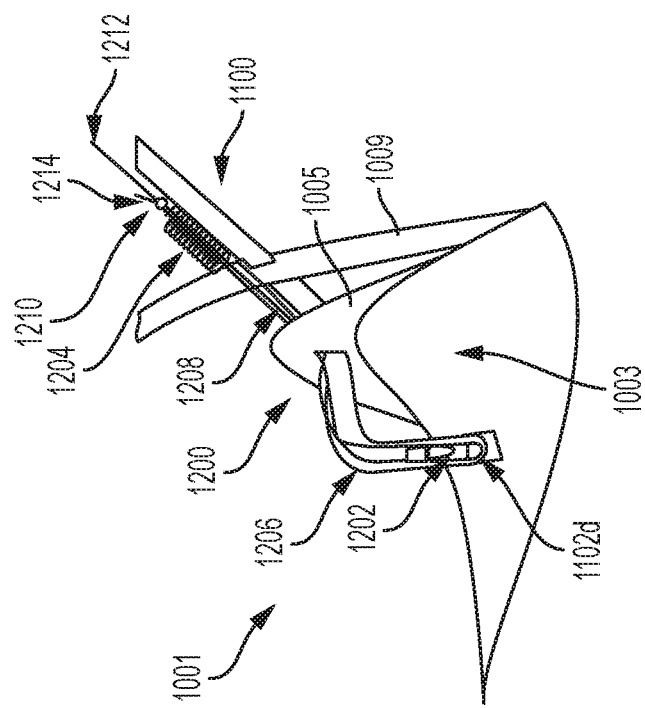
FIG. 8B is another side schematic view illustrating the method of FIG. 8A.
Figure 8A:
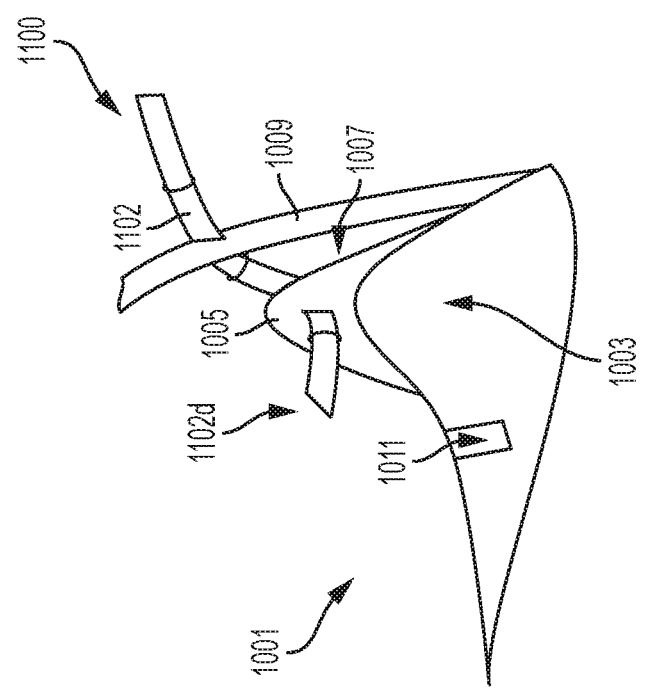
FIG. 8A is a side schematic view illustrating one embodiment of a method of tissue repair in a shoulder joint of a patient.

As shown in FIG. 8A, a hole 1011 can be formed in a glenoid 1003. The bone hole 1011 can be made in any suitable manner. For example, a guide (not shown) can be passed to the surgical site and a suitable instrument (e.g., a drill) can be used to form the hole 1011 at a desired location. Furthermore, in some embodiments, the distal end 1102*d* of the shaft 1102 of the surgical device 1100 can be used to form the bone hole. The bone hole 1011 can have a reduced size as compared to a bone hole that needs to be formed during existing surgical procedures. For example, in at least one embodiment, a diameter of the bone hole 1011 can be about 2 mm. The diameter of the bone hole 1011 can range from about 1 mm to about 4 mm.

As further shown in FIG. 8A, the tissue repair construct 1200 can be advanced into the surgical site. In particular, the distal end 1102*d* of the shaft 1102 of the surgical device 1100 can be passed from the peripheral side of the joint through a capsule 1009 and through a labrum 1005 so as to extend from the labrum 1005 adjacent to the bone hole 1011 as shown in FIG. 8A. Although not shown in FIG. 8A, the shaft 1102 has associated therewith the tissue repair construct 1200 such that a first implant 1202 of the construct 1200 is seated in a longitudinal channel of the shaft 1102 and a second implant 1204 of the construct 1200 is disposed outside of the channel.

The distal end 1102*d* of the shaft 1102 can pierce the soft tissue at a location that is appropriate for repairing the tear 1007 and that is a site of implantation of the second implant 1204. As shown in FIG. 8B, the distal end 1102*d* of the shaft 1102 is advanced towards and into the bone hole 1011 and the first implant 1202 is deployed into the bone hole 1011 from the shaft 1102 in a suitable manner. In some embodiments, a tactile and/or audible feedback may be received once the first implant 1202 is deployed into the bone hole 1011. The delivery device 1100 is advanced distally to the surgical site such that the distal end 1102*d* of the shaft 1102 is disposed on one side of the soft tissue being attached, such as on a glenoid side of the labrum 1005, and the second implant 1204 is disposed on another, opposed side of the soft tissue, such as outside the joint 1001, as shown in FIG. 8B. Thus, the step of actively (i.e., using the delivery device) deploying the first implant 1202 is performed substantially simultaneously with passively (i.e., without a use of a delivery device) deploying the second implant 1204 at a site of its implantation. As the distal end 1102*d* of the shaft 1102 pierces through the capsule and labrum (or, in some procedures, though only the labrum), the second implant 1204 is left behind at the non-joint side of the soft tissue (capsule, in this example) without any intervention. For example, as the distal end 1102*d* of the shaft 1102 moves through the soft tissue towards the bone hole 1011, the second implant 1204 can be caused to be released from a sheath (e.g., sheath 703 of FIG. 6, or any other structure). The second implant 1204 thus remains outside the joint 1001 as the delivery device 1100 is advanced to the surgical site. As also shown, first and second terminal ends 121, 1214 of the flexible element 1206 coupling the implants 1202, 1204 extend from a sliding knot 1210 closing an adjustable loop 1208 formed by the flexible element 1206. The first terminal end 1212 of the surgical device 1200 can extend from the sliding knot 1210 such that the first terminal end 1212 is disposed outside of the joint 1001. It should be appreciated that the second end 1214, wrapped around the first end 1212 (which can be referred to as a "post"), can be much shorter than the first end 1212.

Figure 8D:
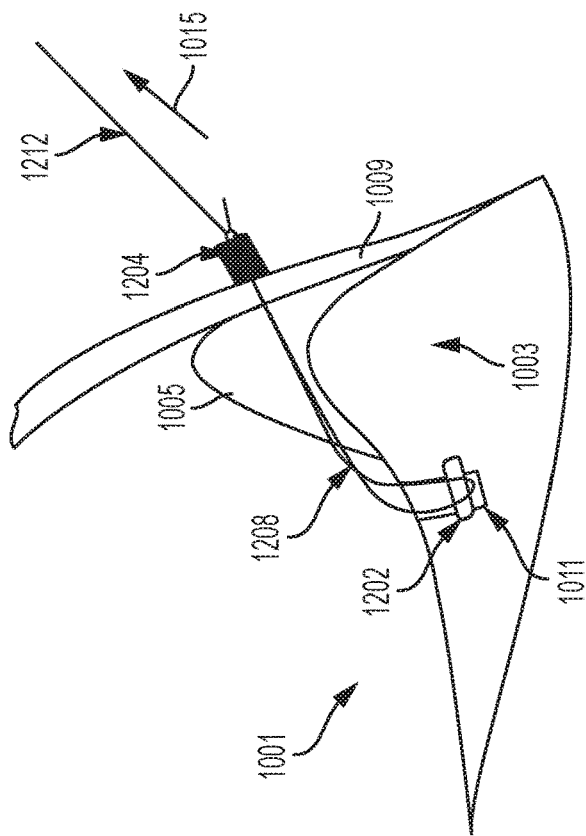
FIG. 8D is another side schematic view illustrating the method of FIG. 8C.
Figure 8C:
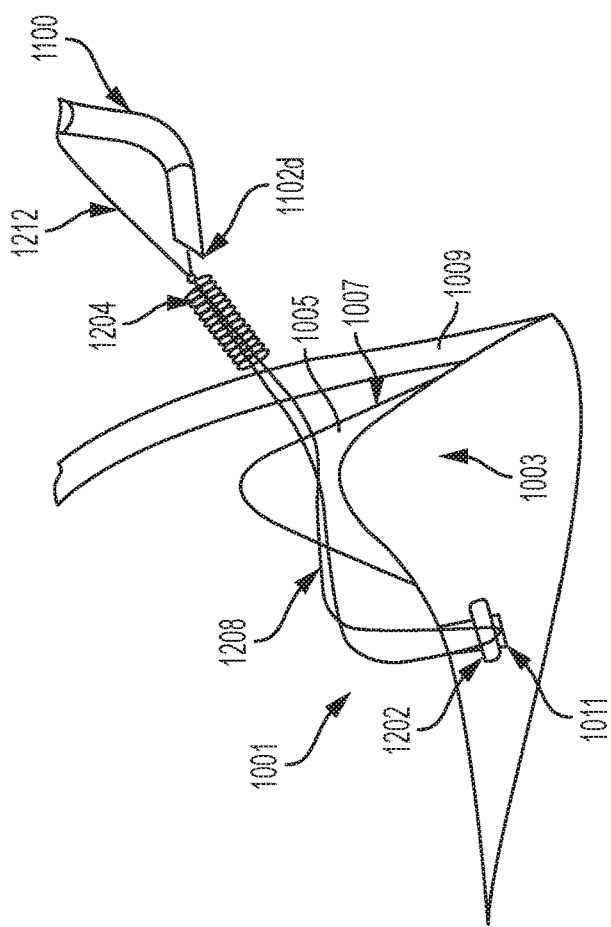
FIG. 8C is another side schematic view illustrating the method of FIG. 8B.

After the first implant 1202 is deployed into the hole 1011, the shaft 1102 of the delivery device 1100 is retracted proximally. As the shaft 1102 is retracted proximally outside of the joint 1001, the second implant 1204 remains positioned at the peripheral side of the capsule 1009, as shown in FIG. 8C. As mentioned above, prior to being deployed, the second implant 1204 can be disposed outside the shaft 1102. However, in some embodiments, before it is passively deployed, the second implant 1204 is seated within a longitudinal channel of the shaft 1102, near the shaft's distal end 1102*d* (e.g., in a shaft's needle). After the distal end 1102*d* of the shaft 1102 pierces the soft tissue and is removed, the second implant 1204 can be passively deployed on the opposed side of the soft tissue, e.g., at the peripheral side of the capsule 1009, in this example.

The delivery device 1100 can be removed from the surgical site and from the joint 1001 such that the first terminal end 1212 of the surgical device 1200 remains outside of the joint 1001. The first terminal end 1212 can then be tensioned, e.g., in a direction shown by arrow 1015 in FIG. 8D. As a result, the flexible element 1206 slides through the sliding knot 1210 (or it can be said that the sliding knot 1210 slides along the flexible element 1206) to decrease a size of the loop 1208 and change a configuration of the second implant 1204. In this way, as shown in FIG. 8D, at least one dimension of the second implant 1204 changes as the second implant 1204 is caused to move towards the first implant 1202, thereby bringing the capsule 1009 and labrum 1005 towards the glenoid 1003 and closing the tear 1007. For example, a length of the second implant 1204 can decrease while its diameter or width can increase, as shown in FIG. 8D. In some embodiments, the second implant 1204 may be additionally pressed or otherwise manipulated to assist in its placement at the implantation site. After the first terminal end 1212 has been tensioned as desired, it can be cut to decrease its length.

Accordingly, a surgical device can be deployed to the surgical site using a procedure involving use of a same device (e.g., delivery device 1100 in FIGS. 8A-8C) for passing a suture and deploying at least one of the implants. The suture passing and anchor deployment are thus performed in the same step. No separate device for passing a suture is required, and no knot tying may be required. These can result in a reduction in a number of steps required to complete a surgical procedure. Also, a bone hole of a reduced size can be created, which reduces impact on the bone.

Figure 9:
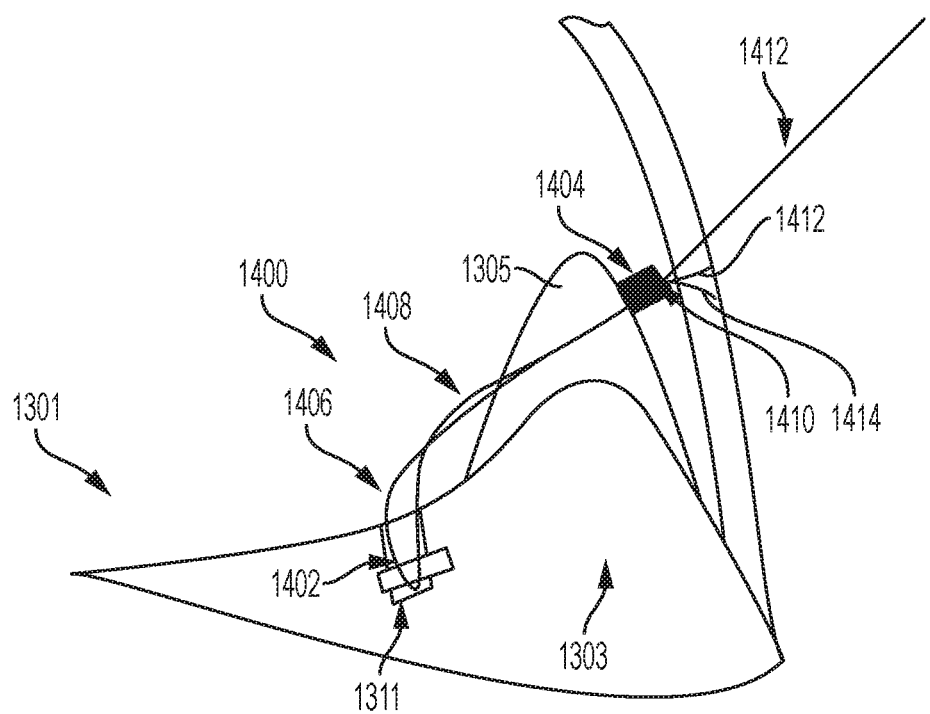
FIG. 9 is a side schematic view illustrating another embodiment of a method of tissue repair in a shoulder joint of a patient.

In the example illustrated in FIGS. 8A-8D, the surgical device is deployed to attach both capsular and labral tissue to the glenoid. FIG. 9 illustrates an example of a surgical tissue repair procedure for attaching only the labral tissue to the glenoid. The surgical procedure of FIG. 9 can be performed on a shoulder joint 1301 in a similar manner to the procedure of FIGS. 8A-8D, and therefore only a result of the tissue repair procedure is shown in FIG. 9. In particular, as shown in FIG. 1, a surgical device 1400 having first and second implants 1402, 1404 coupled via a flexible element 1406 is deployed such that the first implant 1402 is disposed in a bone hole 1311 in glenoid 1303 on one side of labrum 1305. The second implant 1404 is deployed on another, peripheral side of the labrum 1305. First and second free ends 1412, 1414 of the flexible element 1406 are shown to extend from the sliding knot 1410 that closes the loop 1408 formed by wrapping the second end 1414 around a portion of the first end 1412. FIG. 9 shows the surgical device 1400 after the first free end 1412 has been tensioned to cause the flexible element 1406 slide through the sliding knot 1410, a size of the loop 1408 to decrease and thereby change the configuration of the second implant 1404 as the second implant 1404 is brought closer to the first implant 1402.

It should be appreciated that the use of the surgical device described herein to repair a tear in a shoulder joint is shown by way of example only. The surgical device 1100, or any of the other surgical devices for tissue repair in accordance with the described techniques, can also be used to repair a meniscal tear in a knee, or other types of tears or other defects.

As mentioned above, in at least some embodiments, a surgical device described herein can have one or more of its implants coupled to a flexible element via a coupling element. FIG. 10 shows one embodiment of a surgical device 1500 that includes a first implant 1502 and a second implant 1504 having a changeable configuration. The first and second implants are coupled via a flexible element 1506. As shown in FIG. 10, in this implementation, the first implant 1502 can be coupled to the flexible element 1506 via coupling feature 1516, such as a suture tag or any other feature. Although the coupling feature 1516 can have a variety of configurations, in this embodiment, it has a stem element 1522 coupled to the flexible element 1506 and a loop element 1524 coupled between the first implant 1502 and the stem element 1522. The loop element 1524 can pass through the first implant 1502 at a location 1520 of the first implant, as shown in FIG. 10. The stem and loop elements 1522, 1524 can be separate elements coupled to one another, or they can be made from the same suture strand or other element. For example, in the illustrated embodiment, as shown in FIG. 12, the loop 1524 can be formed by a free end of the stem 1522 being passed through (or otherwise coupled to) the first implant 1502 and attached to the stem 1522 at a point 1525 along a length of the stem 1522 (e.g., by being passed through the material of the stem 1522) to thereby create the loop 1524. The coupling feature can have any other configurations. The entire coupling feature 1516 or a portion thereof can be at least partially flexible or conformable, so as to facilitate positioning of the first implant 1512 in a bone hole.

It should be appreciated that the specific shape of the first implant 1512 (similar to the shape of first implant 102 of FIG. 1) is shown by way of example only, as the first implant can have any suitable shape and size. Similarly, the second implant 1504, which can be formed by coupling a suture or other element around a portion of the flexible element 1506, can have any other suitable configuration. As shown in FIG. 10, the flexible element 1506 forms an adjustable loop 1508 closed with a sliding knot 1510, and has first and second free ends 1512, 1514 extending from the knot 1510. It should be noted that, like sliding knot 110 of surgical device 100 of FIG. 1, the sliding knot 1510 is shown in FIG. 10 in a loose configuration for illustration purposes only. In the ready-to-deploy configuration, the sliding knot 1510 formed by wrapping the second free end 1514 around the first free end 1512 is in the form of a pre-tied knot. The first free end 1512 is configured to be tensioned to decrease a size of the loop 1508 and thereby change the configuration of the second implant 1504 and move the second implant 1504 closer to the first implant 1502.

A second implant of a surgical device, such as an implant that is disposed on the opposed side of a soft tissue from an implant that is inserted into a bone hole, can have various configurations. FIG. 11 illustrates an embodiment of a surgical device 1600 that includes a first implant 1602 and a second implant 1604 coupled to one another via a flexible element 1606. As shown in FIG. 11, in this example, the second implant 1604 is a generally cylindrical member having the flexible element 1606 passing therethrough (or otherwise coupled thereto) at locations 1626, 1628 of the second implant 1604, as shown in FIG. 11. In this implementation, the second implant 1604 is at least partially rigid. Similar to first implant 1502 of FIG. 10, the first implant 1602 is coupled to the flexible element 1606 via coupling feature 1616 having a configuration similar to that of coupling feature 1516 of FIG. 10. As in other examples, the first implant 1602 is configured to be implanted into a bone hole on one side of soft tissue, whereas the second implant 1604 is configured to be disposed on the opposed side of the soft tissue. The flexible element 1606 forms an adjustable loop 1608 closed with a sliding knot 1610 (shown in a loose configuration for illustration purposes only), and has first and second free ends 1612, 1614 extending from the knot 1610. In use, the first free end 1612 can be tensioned to decrease a size of the loop 1608 and thereby change the configuration of the second implant 1604 and move the second implant 1604 closer to the first implant 1602.

Each of the first and second implants of a surgical device can encompass one or more respective implants. For example, in some embodiments, the first implant, which is configured to be implanted into a bone, can be in the form of two implants coupled to a flexible element of the surgical device. In at least one implementation, the first implant in the form of two tandem implants can be coupled to the flexible element (e.g., a suture) via a coupling feature. Such a configuration of the first implant allows creating, in use, a toggle effect when the two-piece first implant is implanted into the bone and a free end of the flexible element is tensioned (e.g., pulled) to complete the surgical procedure.

FIG. 12 illustrates an embodiment of a surgical device 1700 that includes a first implant 1702 and a second implant 1704 coupled to one another via a flexible element 1706. In this example, the second implant 1704 is in the form of two separate implants 1702a, 1702b, each of which can be similar to first implant 1502 of FIG. 10. The implants 1702a, 1702 are coupled to the flexible element 1706 via a coupling feature 1716 forming a loop 1724. The loop 1724 can be formed by closing the coupling feature 1716 upon itself in any suitable manner, or in other manners. For example, in at least some embodiments, the loop 1724 can be formed by piercing a material of the coupling feature 1716, e.g., using a luggage tag technique, or any other technique. In some embodiments, the coupling feature 1716 can be coupled to the flexible element 1706 by passing the flexible element 1706 through the material of the coupling feature 1716. The implants 1702a, 1702 are coupled to the loop 1724 in any suitable manner. For example, a portion the coupling feature 1716 forming the loop 1724 can pass through a bore in each of the implants 1702a, 1702 at one or more locations.

The second implant 1704, which has a changeable configuration, can be similar to second implant 1504 of FIG. 10. The flexible element 1706 forms an adjustable loop 1708 closed with a sliding knot 1710 (shown in a pre-tied configuration), and has first and second free ends 1712, 1714 extending from the knot 1710. In use, the first free end 1712 can be tensioned to decrease a size of the loop 1708 and thereby change the configuration of the second implant 1704 and move the second implant 1704 closer to the first implant 1702.

Figure 13:
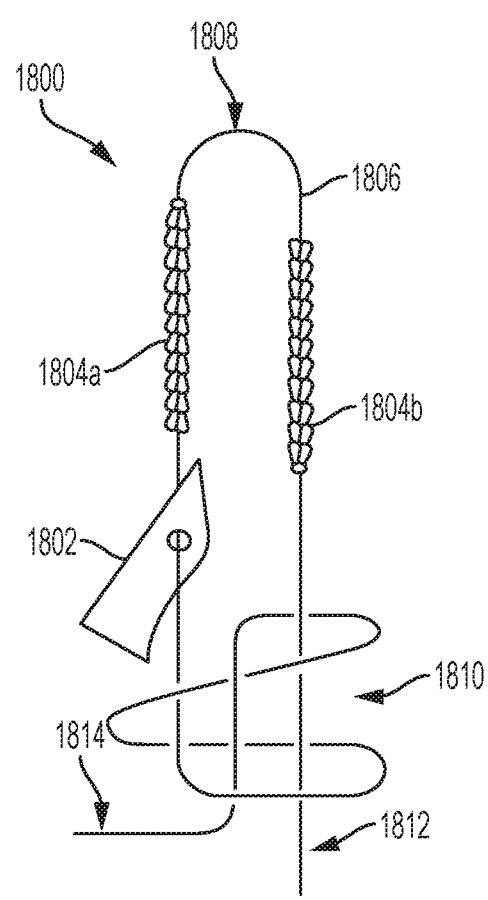
FIG. 13 is a perspective schematic view of still another embodiment of a surgical device.
Figure 14:
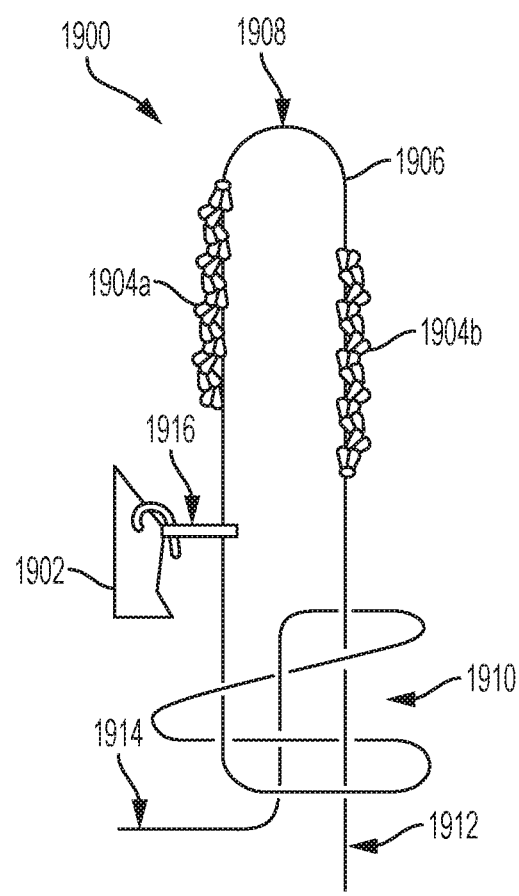
FIG. 14 is a perspective schematic view of still another embodiment of a surgical device.

In some embodiments, a second implant of a surgical device that can have a changeable configuration can be in the form of two or more implants. For example, FIG. 13 illustrates one embodiment of a surgical device 1800 having a first implant 1802 and a second implant in the form of two implants 1804a, 1804b each having a changeable configuration. The first implant 1802 and the second implants 1804a, 1804b can be coupled via a flexible element 1806 forming an adjustable loop 1808 that is closed via a sliding knot 1810. The sliding knot 1810 is formed by wrapping a second free end 1814 of the flexible element 1806 around a first free end 1812 of the flexible element 1806 that is configured to be tensioned. FIG. 14 illustrates one embodiment of a similar surgical device 1900 having a first implant 1902 and a second implant in the form of two implants 1904a, 1904b each having a changeable configuration. The first implant 1902 and the second implants 1904a, 1904b are coupled via a flexible element 1906 forming an adjustable loop 1908 that is closed via a sliding knot 1910 and having first and second free ends 1912, 1914. In this example, the first implant 1902, similar to first implant 1502 of FIG. 10, is coupled to the flexible element 1906 via a coupling feature 1916 (e.g., a suture tag, or any other feature). In some embodiments, the first implant 1902 can be in the form of two or more implants. For example, the first implant 1902 can be similar to first implant of surgical device 1700 (FIG. 12) that is in the form of two implants 1702a, 1702b. Also, in some implementations, the first implant 1902 can be in the form of three or more implants.

Figure 15:
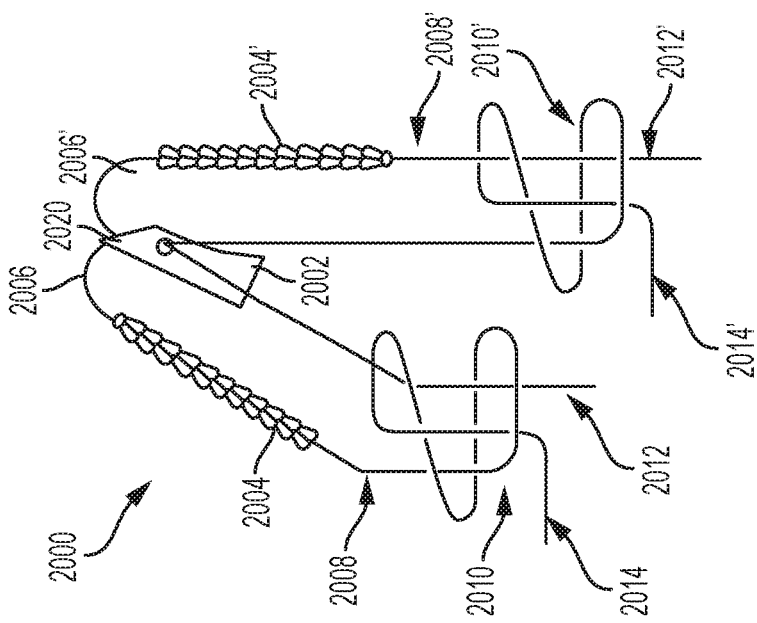
FIG. 15 is a perspective schematic view of still another embodiment of a surgical device.

In some embodiments, a surgical device can include more than one flexible element. The flexible elements can be coupled to each other in various ways, for example, via a first implant that is configured to be implanted into a bone hole. FIG. 15 illustrates one embodiment of a tissue repair construct or surgical device 2000 having first and second flexible elements 2006, 2006' each having components such that each of the flexible elements 2006, 2006' is generally similar to flexible element 106 of FIG. 1. In the embodiment shown in FIG. 15, however, the flexible elements 2006, 2006' are coupled to one another via a first implant 2002. For example, the flexible elements 2006, 2006' can each pass through the first implant 2002 at a location 2020 of the first implant 2002, though the flexible elements 2006, 2006' can be coupled to the first implant 2002 in other various ways. For example, the flexible elements 2006, 2006' can be coupled to the first implant 2002 via one or more separate coupling features. As another variation, each of the flexible elements 2006, 2006' can pass through the first implant 2002 at more than one location of the first implant 2002.

As shown in FIG. 15, the first flexible element 2006 has a second implant 2004 coupled thereto that has a changeable configuration (e.g., similar to second implant 104 in FIG. 1). The first flexible element 2006 forms an adjustable loop 2008 that is closed via a sliding knot 2010 (shown in a loose configuration, before the knot 2010 is pre-tied), and the flexible element 2006 has first and second free ends 2012, 2014 extending from the knot 2010. Similarly, the second flexible element 2006' has a third implant 2004' coupled thereto that has a changeable configuration (e.g., similar to second implant 104 in FIG. 1).

The second flexible element 2006' forms an adjustable loop 2008' that is closed via a sliding knot 2010' (shown in a loose configuration, before the knot 2010' is pre-tied), and the second flexible element 2006' has third and fourth free ends 2012', 2014' extending from the knot 2010'. It should be noted that the free ends 2012', 2014' are referred to as "third" and "fourth," respectively, for description purposes only, as the second flexible element 2006' has two free ends.

The first free end 2012 of the first flexible element 2006 is configured to be tensioned to cause the flexible element 2006 to slide through the sliding knot 2010 and to decrease a size of the loop 2008 and change a configuration of the second implant 2004 to thereby cause at least the second implant 2004 to move towards the first implant 2002. Similarly, the third free end 2012' of the second flexible element 2006' is configured to be tensioned to cause the second element 2006' to slide through the sliding knot 2010' and to decrease a size of the loop 2008' and change a configuration of the third implant 2004' to thereby cause at least the third implant 2004' to move towards the first implant 2002.

The tissue repair construct 2000 can be implanted at a target site, for example, by actively deploying the first implant 2002 at the glenoid on one side of soft tissue, and also actively deploying the second and third implants 2004, 2004' on the opposed side of the soft tissue. However, in some embodiments, the second and third implants 2004, 2004' may be deployed passively.

Figure 16:
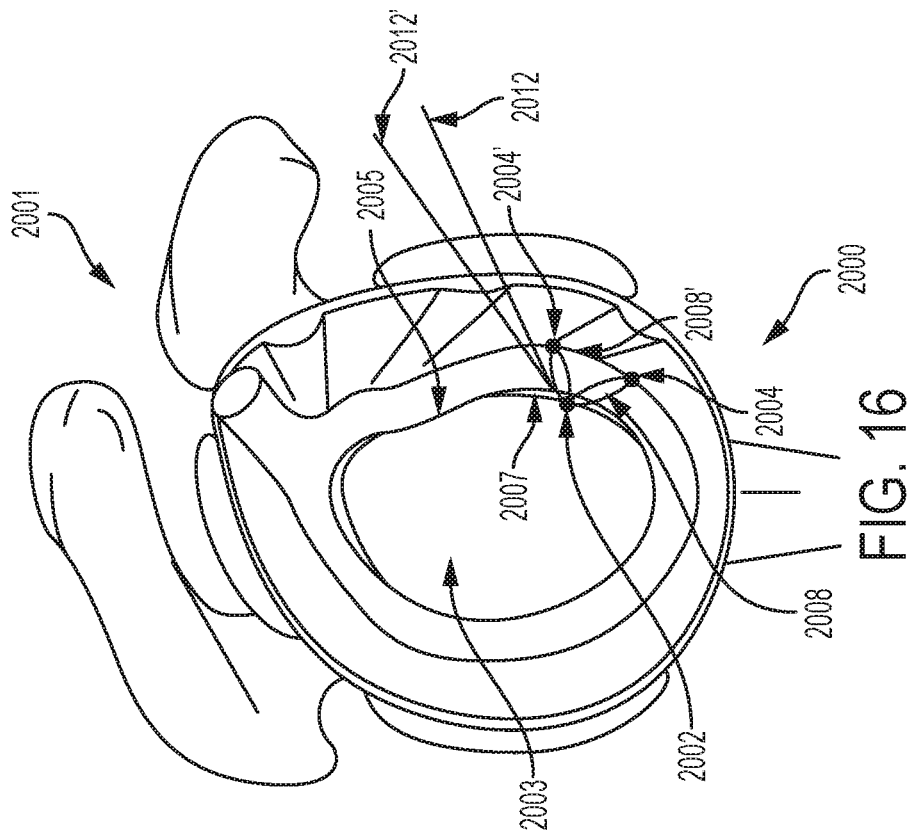
FIG. 16 is a side cross-sectional view of a shoulder joint having the surgical device of FIG. 15 implanted thereto.

FIG. 16 illustrates schematically one embodiment of the surgical device 2000 deployed in a shoulder joint 2001 to repair a tear 2007. The surgical device 2000 can be deployed, using a suitable delivery device. As shown in FIG. 16, the surgical device 2000 is deployed such that the first implant 2002 is implanted in glenoid 2003 on one side of a labrum 2005. The first implant 2002 can be implanted in a hole formed in the glenoid 2003 in a suitable manner. The second implant 2004 coupled to the first flexible element 2006, and the third implant 2004' coupled to the second flexible element 2006', each shown in the changed configuration, are deployed on the opposed side of the labrum 2005 such that respective loops 2008, 2008' span the labrum. The second implant 2004 and the third implant 2004' can be deployed in any order. Also, the second and third implants 2004, 2004' can be deployed in any other with respect to deployment of the first implant 2002. The first terminal end 2012 of the first flexible element 2006 and the third terminal end 2012' of the second flexible element 2006', which have been tensioned to complete deployment of the surgical device 2000, extend from the respective sliding knots that are small and not indicated in FIG. 16.

As discussed above, a surgical device can be deployed in a surgical site using a variety of techniques. FIGS. 8A to 8D above illustrate a technique for deployment of surgical device 1100 that included active deployment of one of implants of the surgical device, whereas another one of the implants was passively deployed. FIGS. 17A-17E illustrate one embodiment of a method for actively deploying both of the implants of a surgical device. In particular, each of the implants associated with a delivery device, e.g., seated in a channel formed at a delivery device's shaft (which can be in the form of a needle), can be deployed using one or more push rods or other mechanisms of the delivery device.

As shown in FIGS. 17A and 17B, a delivery device 2200, having a shaft 2202 with a distal tip 2202*d* that is configured to penetrate through tissue, can be used to pass the distal tip 2202*d* from a glenoid side (2113) through labrum 2105 and capsule 2109 of a shoulder joint 2101. Once the distal tip 2202*d* is on a peripheral side (2115) of the labrum 2105, a second implant 2304 (which can be similar, for example, to second implant 104 of FIG. 1) is deployed, as shown in FIG. 17B. The second implant 2304 can be deployed by, for example, activating a push rod or other suitable mechanism (not shown) of the delivery device 2200. Furthermore, the second implant 2304 can be passively deployed from the channel in the shaft of the delivery device by "catching" or "toggling" on the soft tissue. For example, as the distal tip of the shaft pierces through the soft tissue and is then removed (retracted), the second implant 2304 becomes engaged with the tissue (i.e. is in contact with the tissue) and, because of the implant's shape, interaction with the tissue, or placement within the channel, it becomes disassociated from the delivery device. As shown in FIG. 17B, the second implant 2304 is deployed at the peripheral side 2115 of the labrum 2105.

Figure 17D:
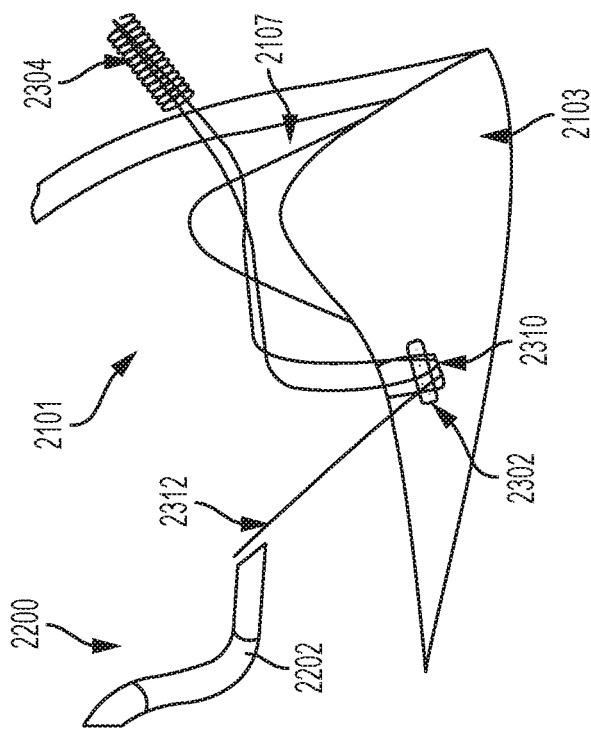
FIG. 17D is another side schematic view illustrating the method of FIG. 17C.
Figure 17C:
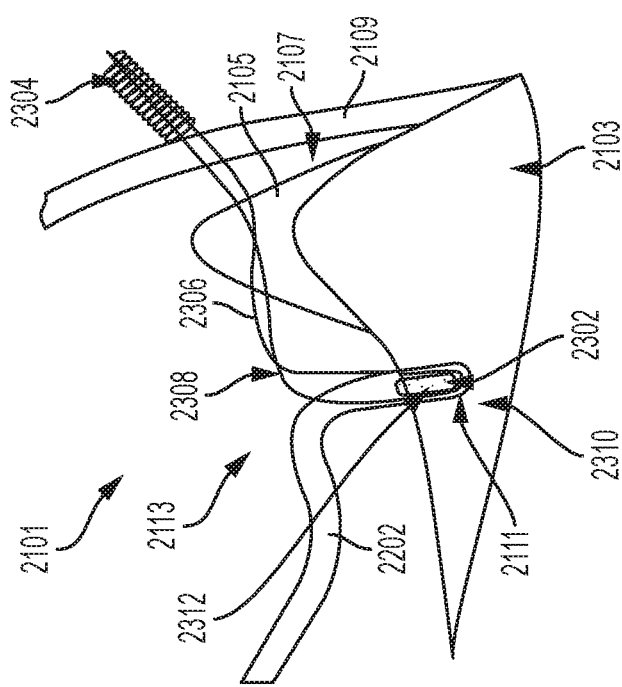
FIG. 17C is another side schematic view illustrating the method of FIG. 17B.
Figure 17E:
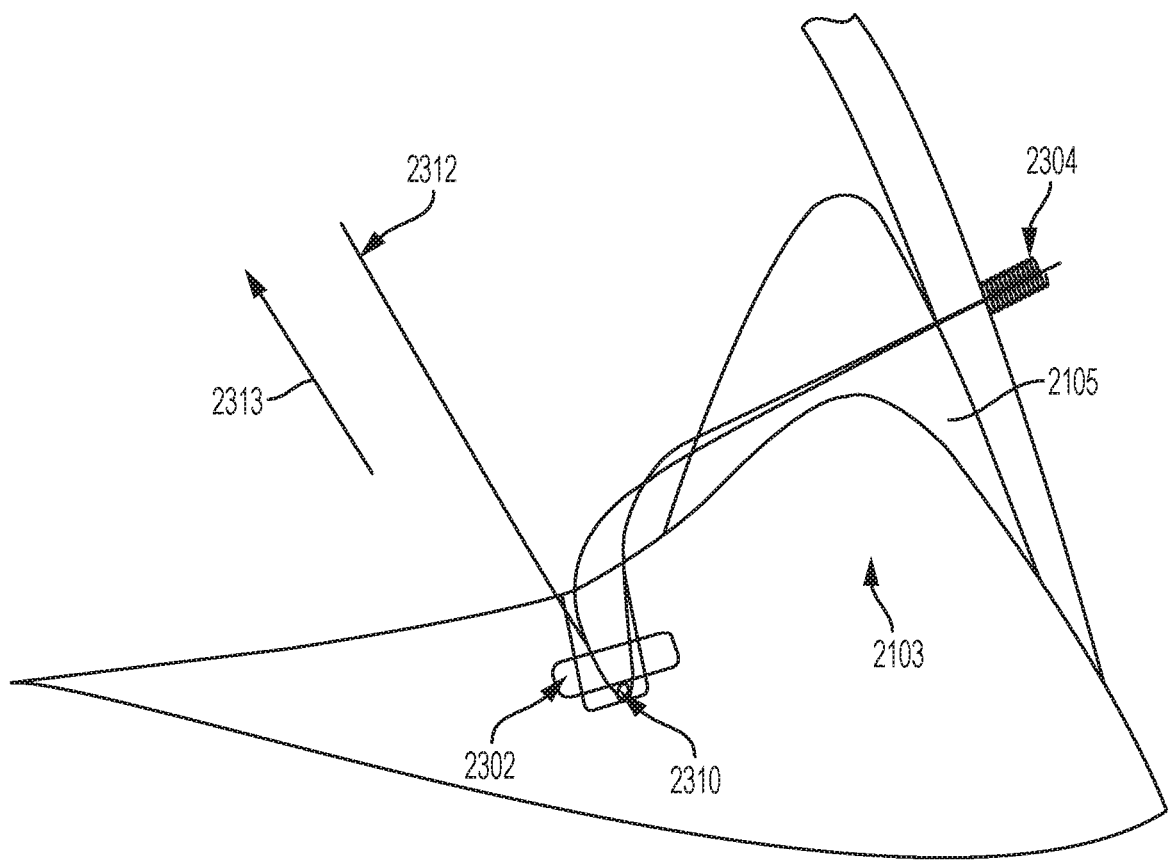
FIG. 17E is another side schematic view illustrating the method of FIG. 17D.

The delivery device 2200 is manipulated so as to retract the distal tip 2202*d* of the shaft 2202 to the glenoid side 2113 where the delivery device 2200 can be activate to deploy a first implant 2302 (which can be similar, for example, to first implant 102 of FIG. 1), as shown in FIG. 17C. As shown, the first implant 2302 is advanced into a previously formed hole 2111 in the glenoid 2103. In some embodiments, however, the hole 2111 can be formed by advancing the distal tip 2202*d* of the shaft 2202 into the bone. The first implant 2302 can be deployed by, for example, activating a push rod or other suitable mechanism (not shown) of the delivery device 2200. Once the first implant 2302 is deployed into the bone hole 2111 as shown in FIG. 17D, the delivery device 2200 is retracted from the joint 2101. In this way, the first implant 2302 is deployed on one side the labrum 2105, whereas the second implant 2304, coupled to the first implant 2302 via a flexible element 2306 forming a loop 2308 closed with a sliding knot, is deployed on the opposed, peripheral side of the labrum 2105. A first terminal end 2312 of the flexible element 2306 is accessible outside of the joint 2101. As shown in FIG. 17E, the first terminal end 2312 can then be tensioned, as shown by arrow 2313, to thereby decrease a size of the loop 2308 and change the configuration of the second implant 2304 (shown in the changed configuration). In this way, at least the second implant 2304 is moved towards the first implant 2302 and the labrum 2105 is thereby moved into the desired location to repair a tear 2107 and thus complete the tissue repair procedure.

In should be appreciated that FIG. 17A-17E illustrate deployment of the second implant 2304 before that of the first implant 2302 by way of example only. For example, in some embodiments where first and second implants of a surgical device are deployed actively, the first implant can be deployed into the bone hole prior to deploying the second implant on the peripheral side of the joint.

Figure 18C:
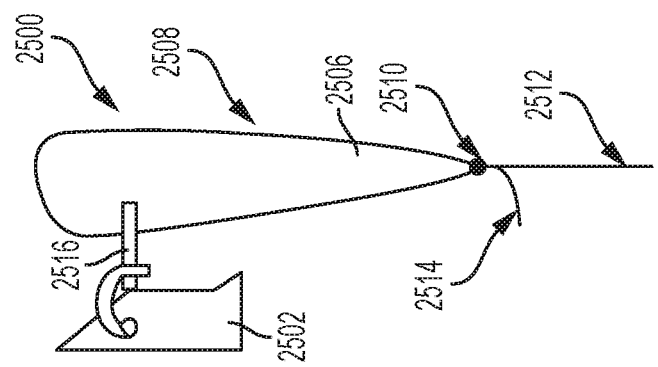
FIG. 18C is a perspective schematic view of another embodiment of a surgical device.
Figure 18B:
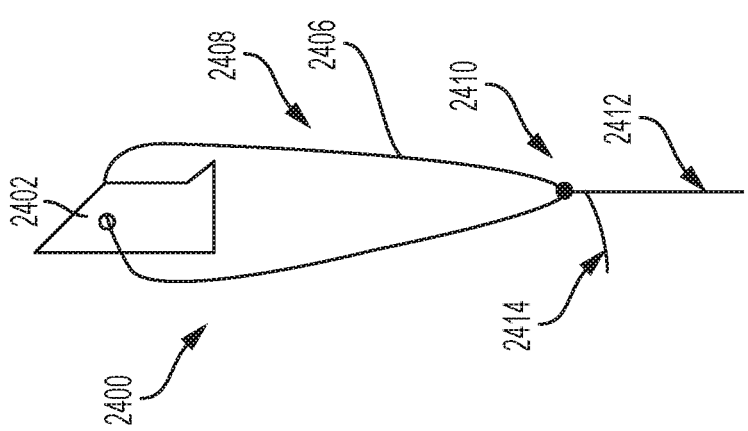
FIG. 18B is another perspective schematic view of the surgical device of FIG. 18A.
Figure 18A:
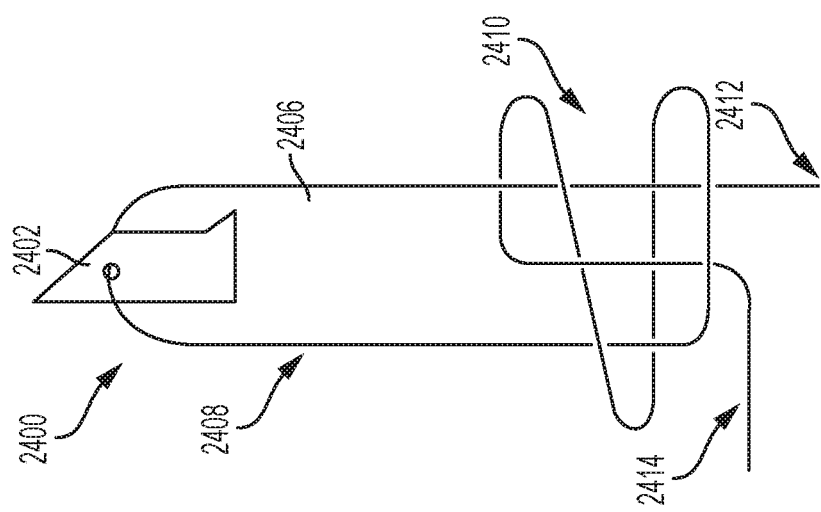
FIG. 18A is a perspective schematic view of one embodiment of a surgical device.

In embodiments described above, a surgical device configured to be deployed at a surgical site to attach tissue to bone includes at least first and second implants. In other embodiments, however, a surgical device can have a single implant coupled to a flexible element that forms a loop by coupling one of its free ends to another via a sliding knot. FIGS. 18A and 18B illustrate one embodiment of a surgical device 2400 having an implant 2402 that is coupled to a flexible element 2406 forming an adjustable loop 2408 that is closed via a sliding knot 2410. The single implant of the device 2400 can be similar, for example, to first implant 102 of FIG. 1. As shown in FIG. 18A, the sliding knot 2410 can be formed by wrapping a second free end 2414 of the flexible element 2406 around a first free end 2412 of the flexible element 2406 that is configured to be tensioned. FIG. 18A illustrates the sliding knot 2410 in a loose configuration, while FIG. 18B shows the sliding knot 2410 in a pre-tied configuration in which the surgical device 2400 is deployed.

An implant of a surgical device can be coupled to a flexible member of the device in many various ways. For example, FIG. 18C illustrates one embodiment of a surgical device 2500 having an implant 2502 that is coupled to a flexible element 2506 via a coupling feature 2516. The coupling feature 2516 can be similar to coupling feature 1516 of FIG. 10, or it can have any other configuration. The flexible element 2506 forms an adjustable loop 2508 that is closed via a sliding knot 2510 (shown in FIG. 18C in a pre-tied configuration) formed by wrapping a second free end 2514 of the flexible element 2506 around a first free end 2512 of the flexible element 2506 that is configured to be tensioned.

Figure 19A:
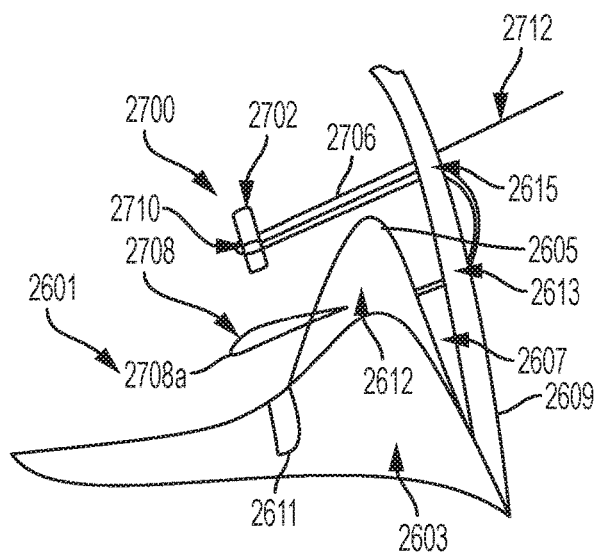
FIG. 19A is a side schematic view illustrating one embodiment of a method of tissue repair in a shoulder joint of a patient.
Figure 19B:
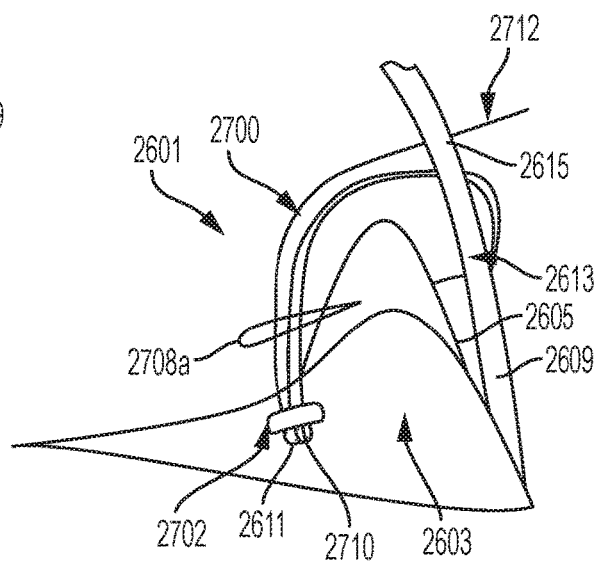
FIG. 19B is another side schematic view illustrating the method of FIG. 19A.
Figure 19C:
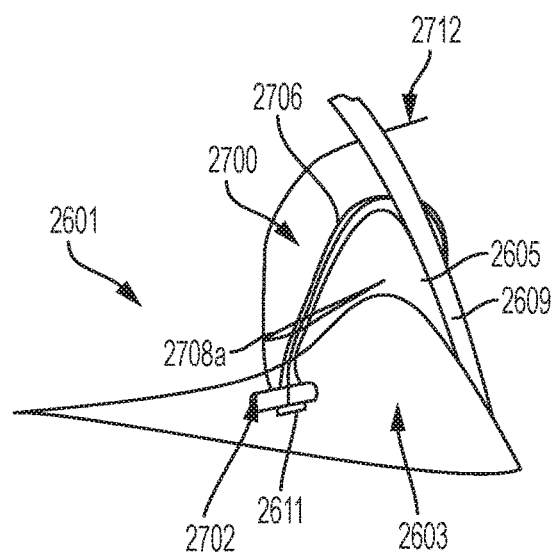
FIG. 19C is another side schematic view illustrating the method of FIG. 19B.

FIGS. 19A to 19C illustrate one embodiment of a surgical method for deploying a surgical device having a single implant at a surgical site. In the illustrated embodiment, as shown in FIG. 19A, a surgical device 2700 can be manipulated (e.g., using a suitable delivery device) such that an implant 2702 coupled to a flexible element 2706 is passed (e.g., by using a piercing needle of a delivery device) from the glenoid side of a shoulder joint 2601 towards the peripheral side through labrum 2605 at a location 2612 and through the capsule 2609 at a location 2613. As also shown in FIG. 19A, after the surgical device 2700 has been passed through the capsule 2609 at the location 2613, the surgical device 2700 can return to the glenoid side, by being passed through the capsule 2609 at a location 2615 to the glenoid side. It should be appreciated that in some surgical procedures the implant of a surgical device can be passed only through the labrum. As further shown in FIG. 19A, the surgical device 2700 is passed through the labrum 2605 and capsule 2609 from the glenoid side towards the peripheral side of the joint and then back through the capsule to the glenoid side such that a portion 2708*a* of a loop 2708 formed by the flexible element 2706 is left in the glenoid space. It should be appreciated that the surgical device 2700 can be deployed in other ways so as to position a portion of the loop 2708 in the glenoid space for receiving the implant. As in other embodiments described herein, the loop 2708 is closed via a sliding locking knot 2710 formed by coupling a second free end (not shown) of the flexible element 2706 around a first free end 2712. The implant 2702 is then passed through the portion 2708*a* of the loop 2708 extending from the labrum 2605 into the glenoid space and advanced into a hole 2611 in the glenoid 2603, as shown in FIG. 19B. The hole 2611 can be pre-formed using a suitable instrument, or, in some embodiments, a distal tip of the delivery device used to deploy the surgical device 2700 can be used to form the bone hole (which can be done substantially simultaneously with advancing the implant 2702 into the bone hole).

Once the implant 2702 is passed through the portion 2708a of the loop 2708 and implanted into the bone hole 2611, the first free end 2712 can be tensioned to thereby decrease a size of the loop 2708 and thus bring the capsule 2609 and labrum 2605 towards the glenoid 2603. In this way, a tear, such as a tear 2607, can be repaired.

Surgical devices described herein can have many variations. For example, a needle at a distal end of a shaft of a surgical delivery device can have various configurations. As mentioned above, the needle can be straight, curved, helical, or it can have any other configuration and the needle's curvature can be selected for passing through tissue at various anatomical locations. The needle can be configured such that, at least in some embodiments, a reduced pusher rod stroke may be achieved.

Figure 20A:
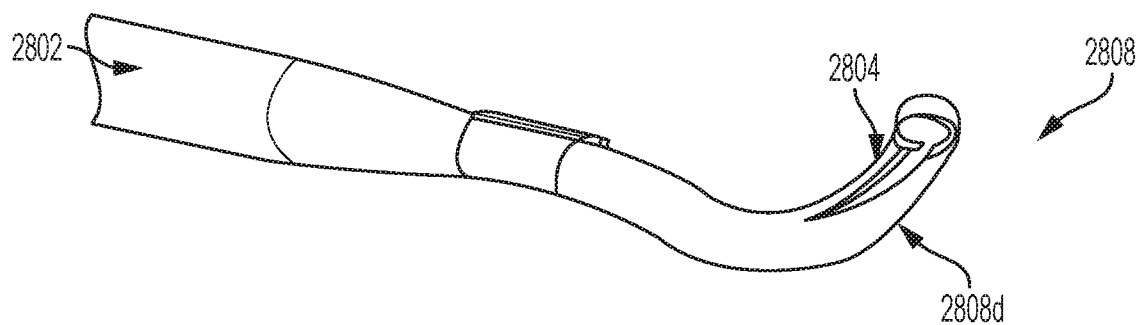
FIG. 20A is a perspective view illustrating one embodiment of a needle of a delivery device.
Figure 20B:
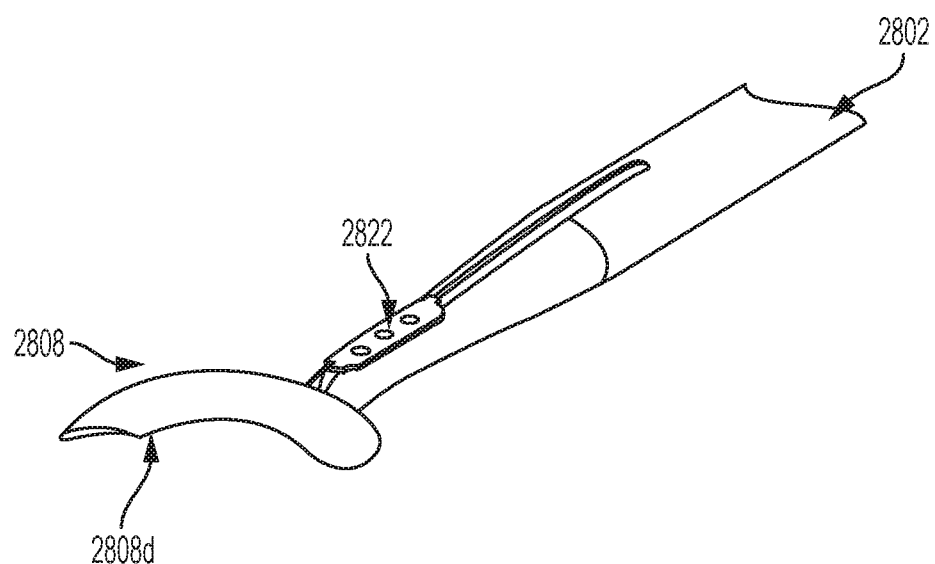
FIG. 20B is another perspective view of the needle of FIG. 20A.

FIGS. 20A and 20B illustrate an embodiment of a needle 2808 of a delivery device having a generally helical shape. The needle 2808 can be coupled distally to a shaft 2802 of the surgical device, or the needle 2808 can be an integral part of the shaft 2802. As shown in FIG. 20A, the needle 2808 can have a longitudinal channel 2804 formed therein along a portion of a length thereof and configured to removably seat one or more implants of a surgical device. Thus, as shown by way of example only, the channel 2804 has an implant 2822 seated therein. The channel 2804 extends between a distal end 2808d of the needle 2808 and terminates at a more proximal point (not shown) on the needle 2808. Any of the delivery devices that can deliver and deploy surgical devices as described herein can have a needle configured similar to the needle 2808 of FIGS. 20A and 20B, or any other needle.

Figure 21:
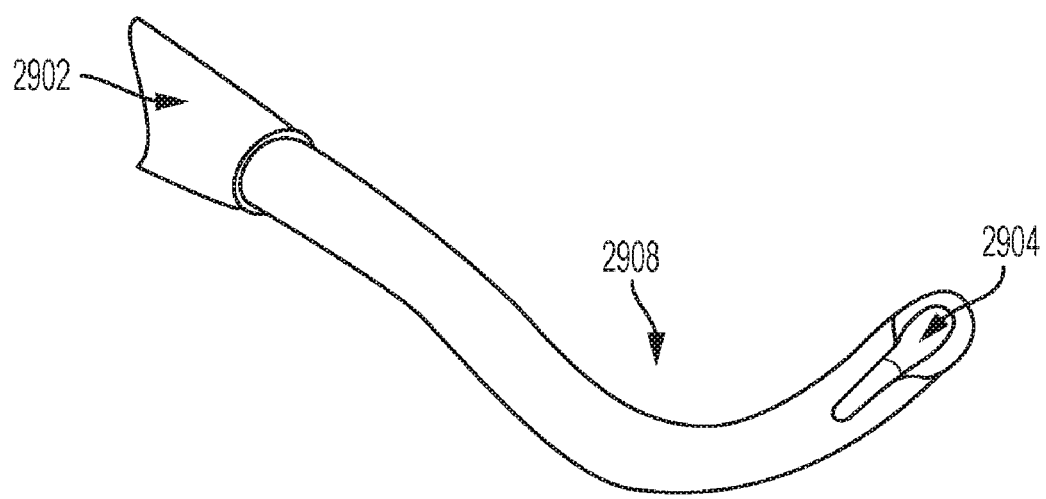
FIG. 21 is a perspective view illustrating another embodiment of a needle of a delivery device.

FIG. 21 illustrates another embodiment of a needle 2908 of a delivery device having a generally corkscrew-like shape. The needle 2908 can be coupled distally to a shaft 2902 of the surgical device, or the needle 2908 can be an integral part of the shaft 2802. As shown in FIG. 21, the needle 2908 can have a longitudinal channel 2904 formed therein along a portion of a length thereof and configured to removably seat one or more implants of a surgical device. Any of the delivery devices that can deliver and deploy surgical devices as described herein can have a needle configured similar to the needle 2908 of FIG. 21.

As mentioned above, implants of a surgical device can have various configurations. A surgical device can include first and second implants, with the first implant configured to be inserted into a bone hole on one side of soft tissue and the second implant configured to be deployed on another, opposed side of the soft tissue. In at least some embodiments, the second implant can be at least partially formed from collagen or other similar polymer.

Figure 22:
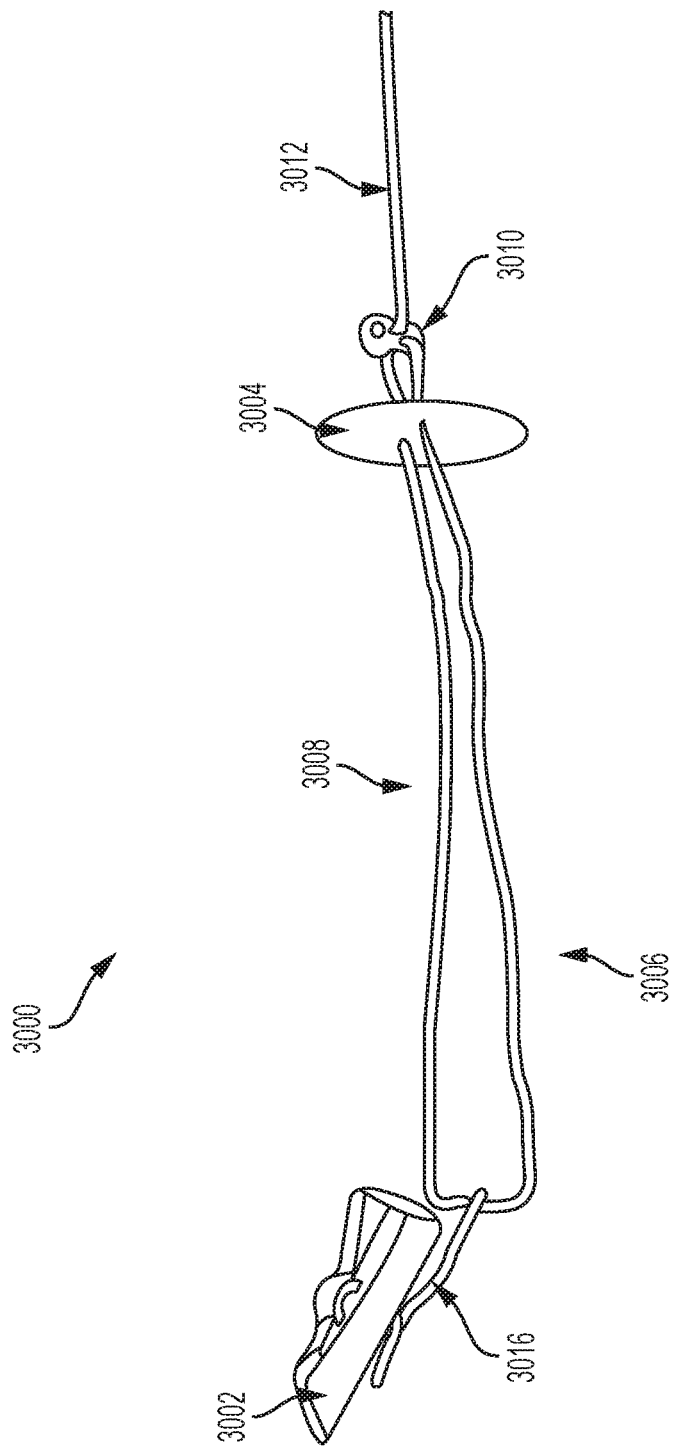
FIG. 22 is a perspective schematic view of an embodiment of a surgical device.

FIG. 22 shows one embodiment of a surgical device 3000 that includes a first implant 3002 (which can be a substantially rigid fixation member) and a second implant 3004 that are coupled via a flexible element 3006 forming a loop 3008 closed via a pre-tied sliding knot 3010 that has a first free end 3012 and a second free end (not shown) extending therefrom. In this embodiment, the second implant 3004, which can be shaped generally as a disk, can be made from collagen. The use of collagen in the second implant can promote tissue healing and regeneration at the surgical site. The tissue can integrate with such an implant. As shown in FIG. 22, in this implementation, the first implant 3002 can be coupled to the flexible element 3006 via coupling feature 3016, such as a suture tag (e.g., round, braided, or flat suture) or any other feature. The coupling feature 3016 can be coupled to the first implant 3002 by passing through one or more bores formed through the first implant 3002. The coupling feature 3016 can form a loop that be coupled to the flexible element 3006. The second implant 3004 can be configured such that its configuration can be at least partially changeable. For example, the second implant 3004 can be at least partially pliable. In at least one embodiment, a diameter of the second implant 3004 can be from about 6 mm to about 8 mm, and a thickness of the second implant 3004 can be about 1 mm. However, the second implant 3004 can have any other suitable dimensions. The first terminal end 3012 can be a tensioning end configured to be tensioned to decrease a size of the loop 3008 and bring the second implant 3004 towards the first implant 3002.

The features illustrated or described in connection with one exemplary embodiment can have any number of modifications and variations that are intended to be included within the scope of the present disclosure. For example, although the systems and methods are described in connection with an arthroscopic shoulder repair procedure, the systems and methods may also be used to repair defects in a knee or a hip of a patient.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical assembly for attaching tissue to bone, comprising:
   a delivery device having a shaft with a tissue penetrating distal tip, the shaft having a longitudinal channel extending through a sidewall thereof along at least a portion of a length of the shaft; and
   a deployable implant construct, comprising:
      a first implant associated with the delivery device, the first implant having a tapered distal end and an asymmetrical proximal end, wherein a protruding edge extends outward from a proximal end face,
      a second implant having a changeable configuration, and
      a flexible element coupling the first and second implants, the flexible element forming an adjustable loop closed with a sliding knot with the first implant and second implant arranged within the adjustable loop, the flexible element passing through the first implant at a position between the distal end and the protruding edge and passing completely through the second implant in a single pass, and having first and second free ends extending from the sliding knot,
      wherein the first free end of the flexible element is configured to be tensioned to decrease a size of the adjustable loop and thereby change the configuration of the second implant, wherein the decrease in the size of the adjustable loop causes the second implant to reduce a length thereof and increase a diameter thereof, and the sliding knot is configured to directly contact the second implant when the size of the loop is decreased.

2. The system of claim 1, wherein the first implant is removably disposed within the channel of the shaft and the second anchor is disposed outside of the channel.

3. The system of claim 1, wherein the first and second implants are removably disposed within the longitudinal channel of the shaft.

4. The system of claim 1, wherein the delivery device comprises a needle having the tissue penetrating distal tip and the longitudinal channel.

5. A surgical method, comprising:
advancing into a surgical site a construct having a first implant, a second implant, and a flexible element forming a loop having a pre-tied sliding knot and coupling the first and second implants;
placing the construct within the surgical site such that the first implant is passed into a bone adjacent to soft tissue and on a first side of the soft tissue, and the second implant and the pre-tied sliding knot are disposed on a second, opposed side of the soft tissue, penetrating the soft tissue with a distal tip of a needle of a surgical instrument having the construct removably associated therewith such that the distal tip is passed from the second side of the soft tissue to the first side of the soft tissue and is advanced into the bone to deploy the first implant into the bone, wherein the second implant is deployed on the second side of the soft tissue as the distal tip passes from the second side to the first side; and
tensioning a loose end of the flexible element extending from the sliding knot to cause the flexible element to slide through the sliding knot to decrease a size of the loop and change a configuration of the second implant to thereby cause at least the second implant to move towards the first implant.

6. The method of claim 5, wherein tensioning the flexible element includes pulling the loose end of the flexible element to thereby lock the sliding knot.

7. The method of claim 5, wherein the second implant changes the configuration such that at least one dimension of the second implant decreases.

8. The method of claim 7, wherein the at least one dimension comprises a length of the second implant.

* * * * *